US007261860B1

(12) United States Patent
Vellinger et al.

(10) Patent No.: US 7,261,860 B1
(45) Date of Patent: Aug. 28, 2007

(54) APPARATUS AND METHOD FOR CENTRIFUGATION AND ROBOTIC MANIPULATION OF SAMPLES

(75) Inventors: John C. Vellinger, Floyds Knobs, IN (US); Rachel A. Ormsby, Edwards, CA (US); David J. Kennedy, Greenville, IN (US); Nathan A. Thomas, Louisville, KY (US); Leo A. Shulthise, Louisville, KY (US); Michael A. Kurk, Georgetown, IN (US); George W. Metz, Sellersburg, IN (US)

(73) Assignee: Space Hardware Optimization Technology, Inc., Greenville, IN (US)

( * ) Notice: Subject to any disclaimer, the term of this patent is extended or adjusted under 35 U.S.C. 154(b) by 770 days.

(21) Appl. No.: 10/270,977

(22) Filed: Oct. 15, 2002

Related U.S. Application Data

(60) Provisional application No. 60/329,865, filed on Oct. 16, 2001.

(51) Int. Cl.
- *A01K 31/19* (2006.01)
- *A01K 41/00* (2006.01)
- *G01N 15/06* (2006.01)
- *G01N 33/00* (2006.01)
- *G01N 33/48* (2006.01)

(52) U.S. Cl. ........................ 422/72; 422/50; 422/68.1; 436/21; 436/43; 436/47; 436/63; 436/174; 436/177; 119/300; 119/302; 119/311; 119/322; 119/323; 119/324; 119/326

(58) Field of Classification Search .................. 422/50, 422/68.1, 72; 436/21, 43, 47, 63, 174, 177; 119/300–328
See application file for complete search history.

(56) References Cited

U.S. PATENT DOCUMENTS

| 3,848,796 | A | * | 11/1974 | Bull ............................... 494/7 |
| 4,776,832 | A | * | 10/1988 | Martin et al. .................. 494/19 |
| 4,812,294 | A | * | 3/1989 | Combs ......................... 422/72 |
| 4,814,282 | A | * | 3/1989 | Holen et al. .................. 436/165 |
| 6,309,875 | B1 | * | 10/2001 | Gordon .................... 435/287.2 |
| 6,361,486 | B1 | * | 3/2002 | Gordon ......................... 494/19 |
| 6,593,143 | B1 | * | 7/2003 | Gordon ......................... 436/45 |

OTHER PUBLICATIONS

Vellinger, John C., Chix in Space Experimental Hardware, American Society for Gravitational and Space Biology, 1989, USA.
The Inovoject Egg Injection System, Embrex, Inc., 2003, embrex.com, USA.

* cited by examiner

*Primary Examiner*—Brian Sines
(74) *Attorney, Agent, or Firm*—Robert H. Eichenberger; Middleton Reutlinger

(57) ABSTRACT

A device for centrifugation and robotic manipulation of specimen samples, including incubating eggs, and uses thereof are provided. The device may advantageously be used for the incubation of avian, reptilian or any type of vertebrate eggs. The apparatus comprises a mechanism for holding samples individually, rotating them individually, rotating them on a centrifuge collectively, injecting them individually with a fixative or other chemical reagent, and maintaining them at controlled temperature, relative humidity and atmospheric composition. The device is applicable to experiments involving entities other than eggs, such as invertebrate specimens, plants, microorganisms and molecular systems.

64 Claims, 18 Drawing Sheets a.

b.

APPARATUS AND METHOD FOR CENTRIFUGATION AND ROBOTIC MANIPULATION OF SAMPLES

This application claims the benefit of U.S. Provisional Application Ser. No. 60/329,865, filed Oct. 16, 2001.

STATEMENT REGARDING FEDERALLY SPONSORED RESEARCH OR DEVELOPMENT

The U.S. Government may have a royalty-free license to use, and to authorize others to use on its behalf, these data for Government purposes, and may be relieved of all disclosure prohibitions and assume no liability for unauthorized use of these data by third parties, as provided for by the terms of NAS 296022 awarded by NASA.

BACKGROUND OF THE INVENTION

1. Field of the Invention

This invention relates generally to a device and its related subsystems for robotically incubating eggs or other samples under various conditions of inertial acceleration and precisely controlled environments. More specifically, the preferred embodiment relates to an apparatus or device and method for the incubation of vertebrate eggs in a controlled environment in which centrifugation is provided as a source of inertial acceleration, especially for experiments performed on orbiting spacecraft.

2. Description of the Prior Art

Methods for the incubation of poultry eggs are abundant in the poultry industry. In particular, commercial incubators manufactured by G.Q.F. Manufacturing Company of Savannah, Ga., for example, are routinely used. Typically, these commercial incubators include one or more rectilinear trays that hold multiple eggs, wherein the trays are mounted on an axle that allows for automatic rotation of the trays.

Devices for the incubation of eggs on spacecraft have been used historically, and Vellinger et al. teaches a method for holding hen eggs in a controlled environment during orbital space flight and a manual means of adding fixative to preserve them for analysis upon return to laboratories on Earth. Vellinger, et al. however provides no robotic means for rotating eggs, either individually or on a centrifuge, and further provides no method or apparatus for controlling the internal environment of the housing algorithmically; no method or apparatus for proper vapor containment and exhaust; no double contaminant venting; and no two-level pass-through electronics. Additionally, it provides no robotic means for chemically fixing eggs for preserving them for analysis upon return to Earth. Likewise, it provides no fire-suppression system for the automatic extinguishment of fires, smoldering matter, and thermodegradation in electronic racks.

Poultry and avian research laboratories could greatly increase their experimental throughput and improve upon statistical value of data by being able to process hundreds of developing avian embryos without operator intervention. Therefore, the need exists for a device that provides for egg processing without operator intervention. A special need exists for such devices specifically designed for avian development research aboard spacecraft.

SUMMARY OF THE INVENTION

Accordingly, the present invention is directed to apparatus and methods for robotically incubating eggs or other entities under various conditions of inertial acceleration, and, more particularly, for incubating vertebrate eggs in a controlled environment in which centrifugation is provided as a source of inertial acceleration, especially for experiments performed on orbiting spacecraft. It should be understood that the invention relates not only to the processes involved in the incubation of eggs, but also the processes involved in the experimentation performed on samples or entities other than eggs, including but not limited to, invertebrate specimens, plants, microorganisms, and molecular systems. All of these entities can properly be termed samples and can be used in place of the eggs described herein. However, for the sake of brevity and for ease of understanding, the description of the apparatus and methods employed in the present invention will be made with reference to eggs, particularly of the avian variety, as this is a common sample for experimental study.

Experiments involving embryonic development of birds must be built on the natural conditions under which avian eggs normally develop. Eggs, whether in nature, or in the laboratory, are typically rotated periodically each day (either by the mother bird or by the experimenter) so as to prevent the yolk from settling, to exercise the embryo, and so forth. The fracture modulus of the egg shells establishes the force that may be applied to immobilize and to inject the eggs. Forces greater than the fracture modulus will break the egg shell—an undesired occurrence. Experiments in which inertial acceleration is studied as a variable require that all other conditions should be held constant. The present invention achieves this condition by producing two values of inertial acceleration in a single, environmentally controlled container, enabling one set of inertial acceleration conditions to be the control group, and another set of inertial acceleration conditions to be the experiment group.

The apparatus enables the experimenter to perform all of the functions typically conducted on developing eggs, namely: (a) rotating eggs on a natural or an experimental schedule; (b) rotating eggs as individuals; (c) holding eggs so that shells are not broken during processing; (d) injecting specified volumes of fluid in each egg on each egg's programmed schedule.

In the preferred embodiment, the apparatus comprises one or more carousels (or other mechanical transporters) for transporting or holding samples; a plurality of innovative holders that immobilize the eggs sufficiently firmly to allow injection and/or rotation under computer control; a chemical robot constituting an injection station; a control computer; and control software. In general terms, the carousel comprises around its periphery a plurality of innovative holders for individual eggs. The egg holders are rotated through a programmed number of degrees at programmed times during an experiment. The carousel transports each egg to a chemical robot station for injection. In operation, eggs to be incubated are placed in the egg holders located on the carousels. A computer program is initiated. The carousel may or may not rotate continuously in a single plane. At specified times the computer program initiates rotation of each egg holder through (typically) 180° in a vertical plane. At specified times the computer program instructs specific egg loci to stop at the chemical robot, which then injects the egg with a specified volume of fluid. These processes are repeated on a schedule set by the operator without operator intervention.

Alternative embodiments include devices having a linear sample translator instead of a carousel. In one embodiment the device is adapted to function in space flight in low gravity. In another embodiment the individual egg holders are fabricated with windows to permit candling (examining an egg in the presence of a powerful backlight) and/or aeration. In another embodiment the operating computer is under remote control and reprogrammable at any time. In another embodiment egg holders are replaced by vials capable of containing fluids for the cultivation of organisms.

In one embodiment, a carousel having a radius of approximately 20 cm contains a plurality of machined plastic cylinders approximately 6 cm high and 2 cm in diameter, and having external gear teeth. A motor operates the translation and rotation mechanisms via, typically, a series of gears. The entire device may be, at the user's discretion, operated in an enclosure with control of temperature, atmosphere, and humidity. An external or an internal 16-bit computer may be used. When constructed of appropriate materials, the device requires only cleaning to be reliable and safe. In one embodiment the entire device is constructed of non-flammable materials. Many embodiments include the following typical physical parameters (approximate):

Number of eggs accommodated: Total of 36 (18 per each carousel)

Power requirements: 100 Watts typical, 130 Watts max.

Operating computer: x-486 based, PC-104 form factor

Range of carousel speeds: 0 to 100 rpm

Time required per egg injection: 4 minutes

Range of egg-rotation intervals: 1 to 6 hours

The devices according to the present invention can be viewed, in the preferred embodiment, as an avian development facility ("ADF"). The ADF uses novel mechanical technology to form a biomechanical (egg-machine) interface. All experimenter functions can be carried out without operator intervention. All procedures can be programmable and customizable to individual eggs. The devices according to the present invention provide many advantages over the prior art, including but not limited to remote around-the-clock operation, not just in avian and poultry research laboratories but also in the low-gravity, long-duration, mass-constrained, no-operator conditions of orbital space flight. The innovation is useful and assured to operate, for example, on the U.S. space shuttle orbiters, the International Space Station, and the MirCorp Space Station. An additional advantage is the use of the device in spaceborne experiments other than those involving avian eggs by the use of specimen containers instead of eggs in the rotating individual stations. In a specific embodiment the innovation affords 1-g control and low-gravity exposure when used in orbital space flight.

BRIEF DESCRIPTION OF THE DRAWINGS

The teachings of the present invention can be readily understood by considering the following detailed description in conjunction with the accompanying drawings, in which.

DETAILED DESCRIPTION OF THE PREFERRED EMBODIMENT

While the present invention will be described more fully hereinafter with reference to the accompanying drawings, in which particular embodiments and methods are shown, it is to be understood from the outset that persons of ordinary skill in the art may modify the embodiments of the invention described herein while achieving the functions and results of this invention. Accordingly, the descriptions which follow are to be understood as illustrative and exemplary of specific embodiments within the broad scope of the present invention and not as limiting the scope of the invention. In the following descriptions, like numbers refer to similar features or like elements throughout.

As stated, it should be understood that the invention relates not only to the processes involved in the incubation of eggs, but also the processes involved in the experimentation performed on samples or entities other than eggs, including but not limited to, invertebrate specimens, plants, microorganisms, and molecular systems. All of these entities can properly be termed samples and can be used in place of the eggs described herein. However, for the sake of brevity and for ease of understanding, the description of the preferred embodiment of the apparatus and methods employed in the present invention will be made with reference to eggs, particularly of the avian variety, as this is a common sample for experimental study.

The present invention is a device 10 for the safe and reliable incubation of eggs (avian, reptilian, etc.) and the imparting of inertial accelerations on them and the automatic delivery of injectable chemicals to eggs or other samples in their containers. The device 10 includes several subsystems for performing different functions, including (a) enclosing the mechanisms of the device 10; (b) rotating various carousels 30; (c) holding individual egg samples 12; (d) injecting liquids into individual egg samples; (e) controlling the internal environment; (f) controlling the conduct and movement of the components and subsystems by computer; (g) managing toxic vapors that may be created as a result of experimentation; and (h) providing built-in fire suppression.

Figure 1:
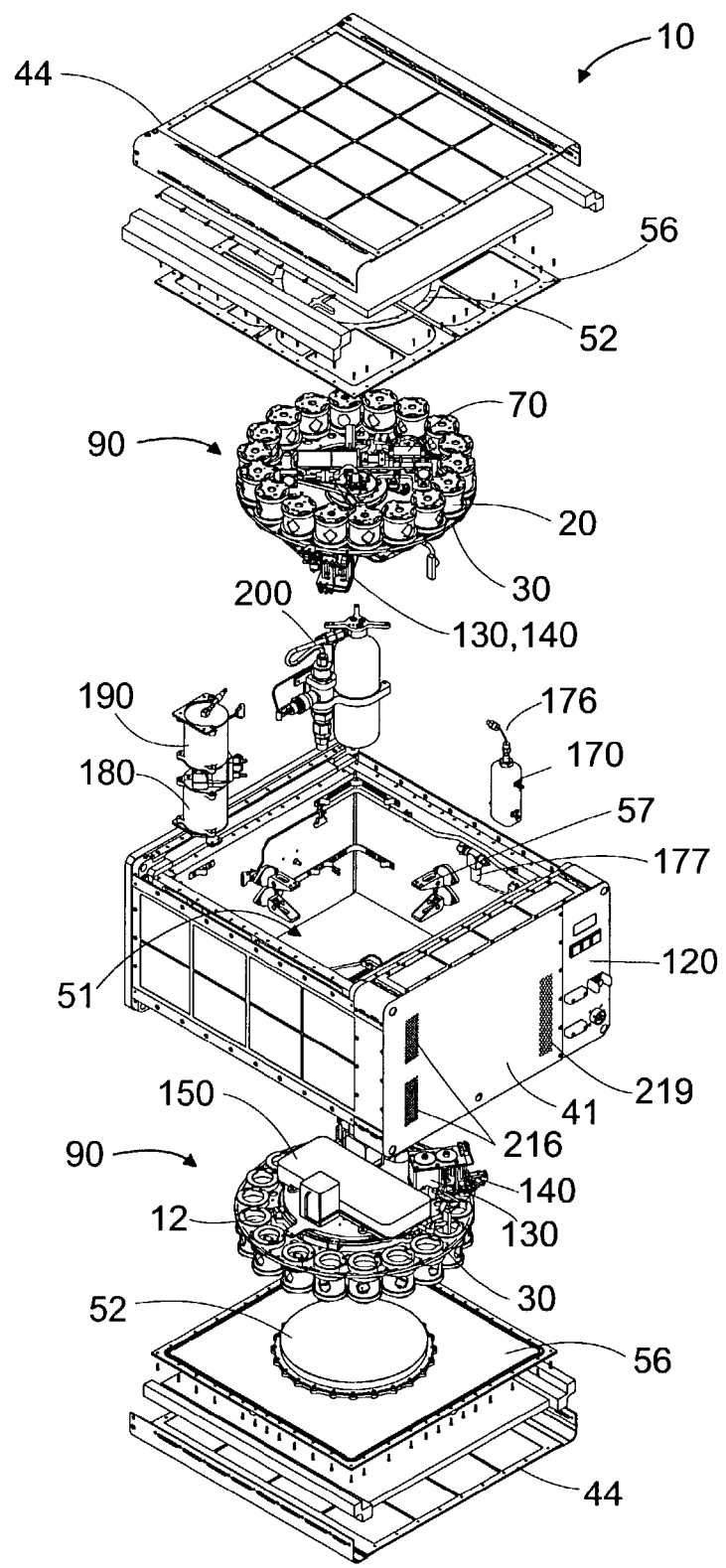
FIG. 1 is an exploded isometric view of the mechanical components according to a preferred embodiment of the present invention.

In the preferred embodiment shown in FIG. 1, egg samples 12 are contained in eighteen containers known as egg holders 20 in each of two carousels 30. The preferred embodiment comprises two separate and independent carousels 30. Because all the relevant structures for the carousels are identical, only one carousel will be described herein, it being understood that the relevant structures for each carousel will be the same. Although the device and methods will be more fully described below, in general the carousels 30 of the preferred embodiment are rotated at speeds between 0 and 100 rpm to impart inertial accelerations between 0 and 3 times that of Earth's gravity. Obviously, these parameters are variable, and higher or lower speeds of rotation are possible with the invention. Egg holders 20 are rotated at a rate compatible with the regular change of orientation effected by mother birds or commercial egg incubators. At specific times specified by an investigator 100 or computer 120 an algorithm is implemented that causes injection system 130 to position an egg 12 in its egg holder 20 over an injection needle 140 which is connected to a reservoir 150 containing injection fluid. The injection fluid may be a fixative for the preservation of morphology at the cellular level, a drug to influence the course of development, or a chemical for the extraction of biological substances like mRNA, to name but a few examples.

Figure 2:
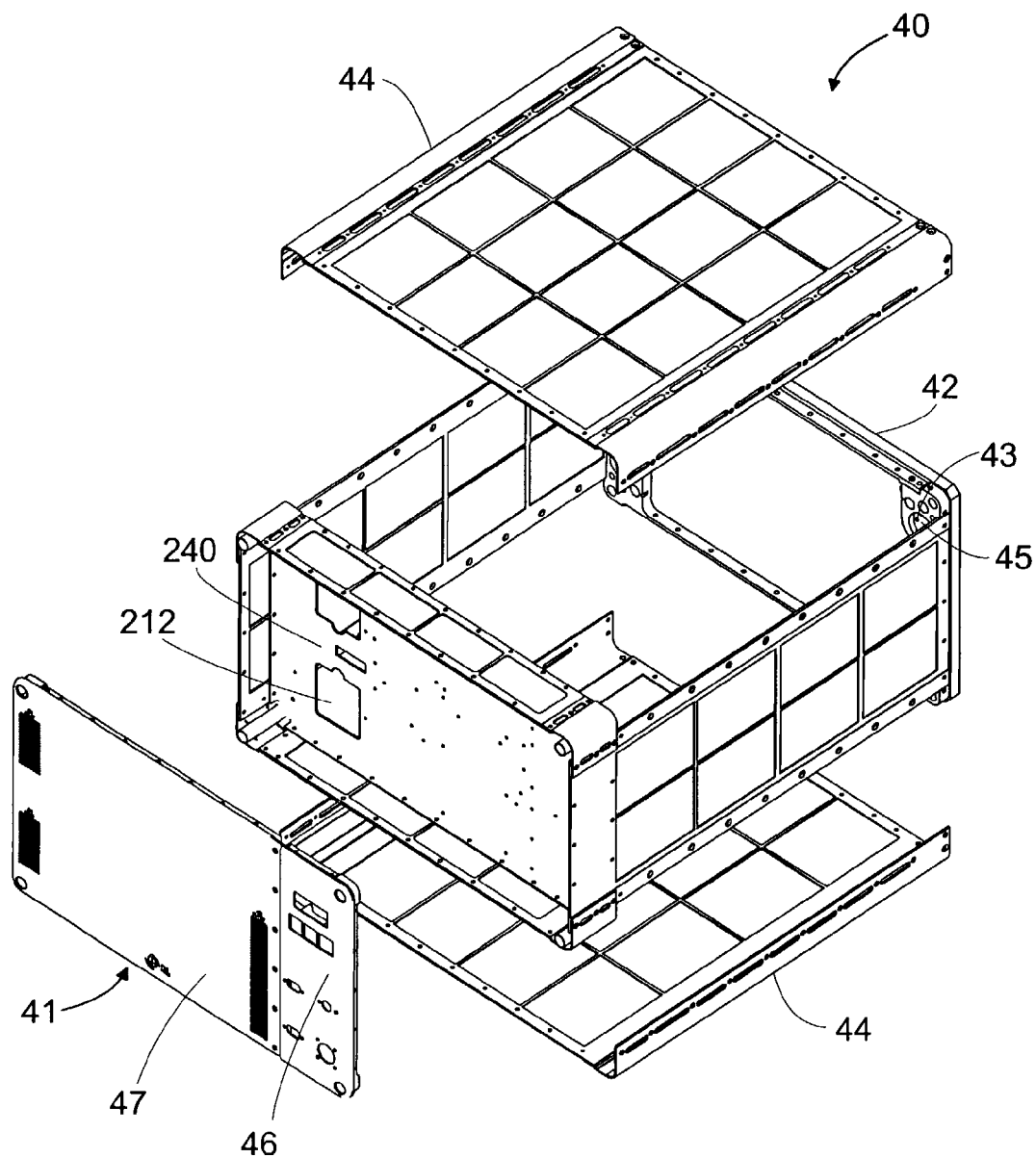
FIG. 2 is an exploded isometric view of the outer containment housing.
Figure 3:
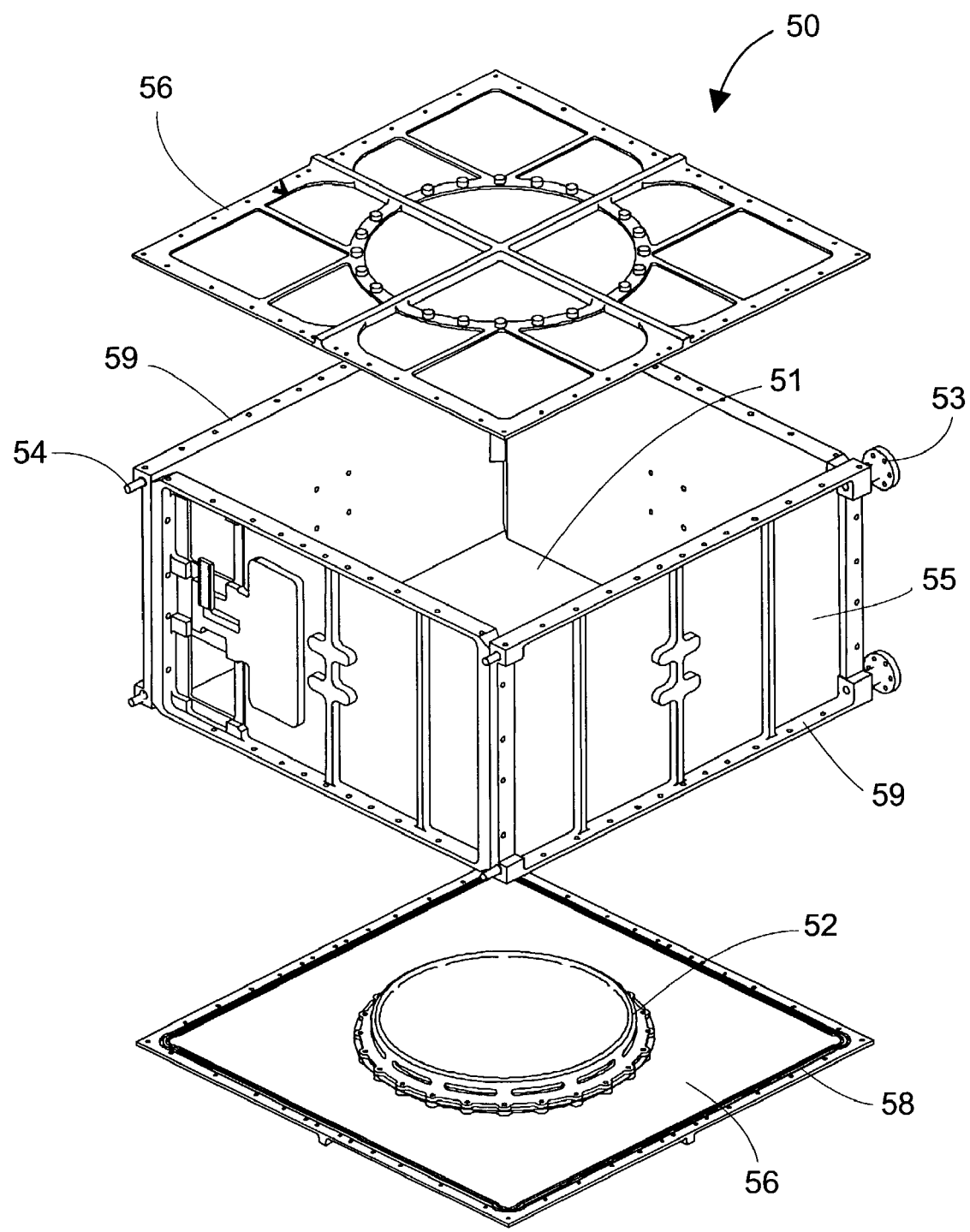
FIG. 3 is an exploded isometric view of the inner containment housing.

FIGS. 1, 2, and 3 show in exploded form the major components of the device 10. The exterior housing consists of two subassemblies, an outer housing 40 and an inner housing 50. The outer housing 40, shown in FIG. 2, provides the structural support walls 42, protective lids 44, containment of the primary electronics 46, and the mounting interface from the device 10 to the space vehicle avionics wire tray.

The inner housing 50 shown in FIG. 3 is designed around the function of the ADF specimen volume 51 and the space within the inner housing 50 that contains the incubation environment. It is regulated by temperature, humidity, carbon dioxide, and oxygen. Space flight requires that systems be capable of withstanding a pressure differential of +/−3 psi, as this differential can experienced at various times during the space mission. Therefore, a vent system 52 is designed so the inner housing 50 can develop a maximum worst-case pressure differential of 3 psi with respect to ambient air pressure across its surface. Likewise, the inner housing 50 is designed to withstand a 3 psi pressure differential. The added structure needed to withstand the pressurization requirements inherently makes the inner housing 50 a rigid body. This rigidity is utilized to reinforce the outer housing 40 and electronics volume via structure pins 53 in the front and back of the ADF unit, with the majority of the mass for the housing system located in the inner housing 50.

FIG. 3 shows an exploded view of the inner housing 50 with the front structure pins 54 and rear structure pins 53 that tie the housing together. The inner housing 50 is composed of four side panels 55, two lids 56, four front structure pins 54, and four rear structure pins 53. In the preferred embodiment, the inner housing 50 provides a specimen volume 51 of approximately 14.8 inches long by 15.1 inches wide by 8.6 inches tall. This yields a specimen volume 51 of approximately 1,925 cubic inches. The inner housing 50 provides mounting and structural supports 57 for the following: (a) environmental control subsystems (to be described below) within the specimen volume 51; (b) the centrifuge systems (that is, the carousels 30 and their related structures); and (c) some of the electronics.

The secondary structural integrity of the inner housing 50 is created by the top and bottom lids 56. In the preferred embodiment, the lids 56 are manufactured from a ⅜" sheet of 6061-T6 aluminum. Two O-ring grooves 58 in each of the lids 56 hold EPDM O-rings that seal along the top and bottom of the inner housing 50 frame. Each lid 56 is fastened to the inner housing flange 59 via a set of 48 #4-40 socket cap fasteners. This accomplishes the structural mounting of these plates as well as the clamping force needed to keep the O-rings sealed under 3 psid (psi differential). The plate stiffness of the lids 56 reinforce the inner housing 50 structure.

The inner housing 50 is cantilevered from the structural support walls 42 of the outer housing 40 by the set of four rear structure pins 53 which penetrate structure pin holes 43 (FIG. 2). In this preferred embodiment, these pins are manufactured from Ti6AL-4V titanium. Each structure pin is fastened to the back plate of outer housing 40 by six #6-32 flathead fasteners. The inner housing 50 is affixed to each structure pin 53 by a ¼-20 socket cap fastener. Both the structural support walls 42 and the inner housing 50 have a counter-bored volume 45 for the structure pin 53 interface, which minimizes bending forces and stresses in the structure pins 53.

Figure 4:
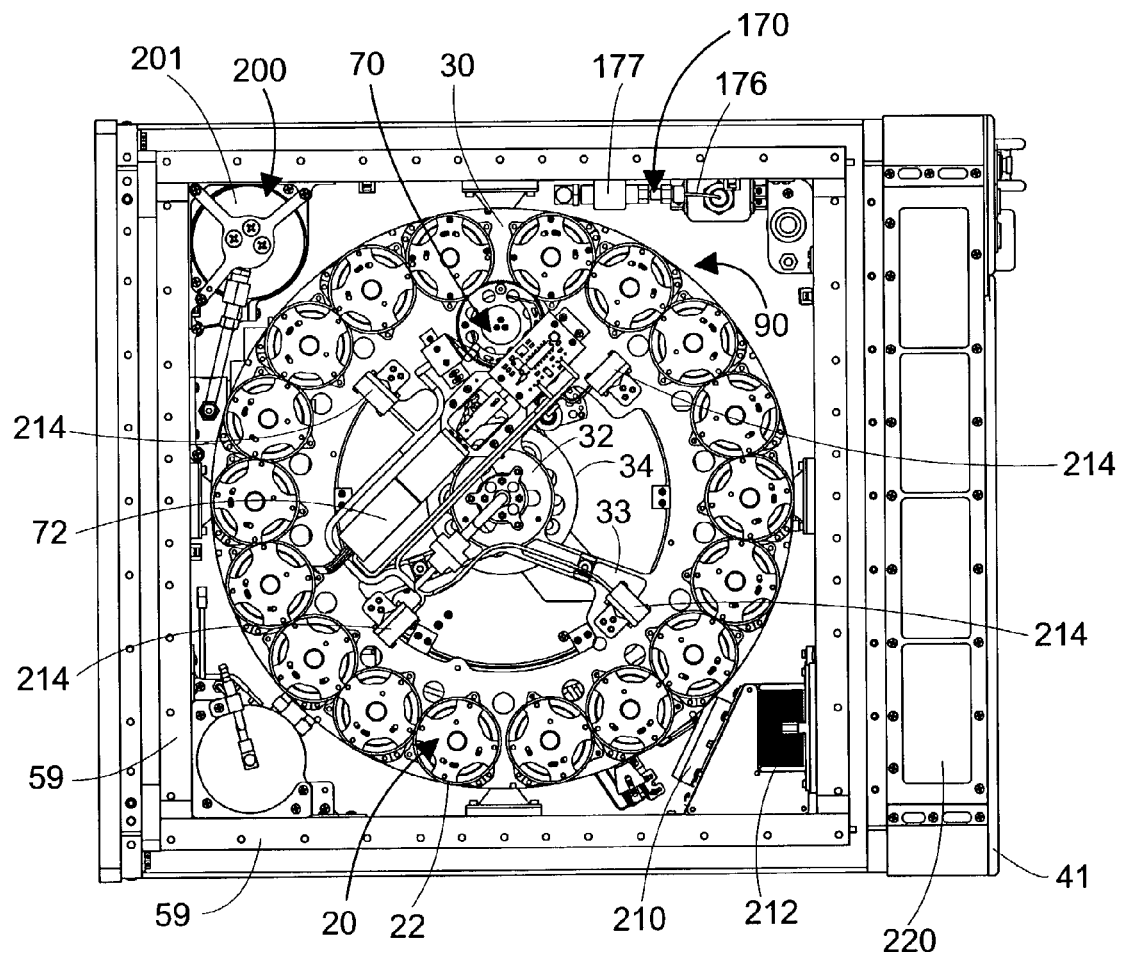
FIG. 4 is a plan view of one of the centrifuges and the associated mechanics on the interior of an embodiment of the invention.

The device 10 further comprises one or more centrifuge systems 90 shown in FIG. 1 as it fits into the device 10, and shown in detail in FIG. 4, which allows an investigator to expose egg samples 12 to low or micro-gravity situations and provide side-by-side experiment controls within an atmospherically identical environment. In the preferred embodiment, two carousels 30 are included, each identical to the other, and each completely independent from the other. The reason for two completely independent carousels 30 is so that one carousel 30 can be the control group (to which is applied a simulated 1 G inertial acceleration to simulate that of earth), while the other carousel 30 can be subjected to other inertial accelerations (in the preferred embodiment, the experimental inertial acceleration is low or micro gravity). Both sets of egg samples 12 in the carousels 30 are exposed to the same uncontrolled variables such as launch accelerations and landing vibrations. This produces an environment in which microgravity is the only parameter different between the test and control eggs. Such isolation of one variable enhances the reliability of the experimental results.

The centrifuge system 90 further comprises two subsystems: the carousel drive subsystem 60 and the egg turning subsystem 70. FIG. 4 illustrates one centrifuge system 90 and its components. The carousel drive subsystem 60 (FIG. 5) enables an infinite number of inertial acceleration environments to be applied to the egg samples 12 in the carousels 30. Most importantly in the preferred embodiment, the carousel drive subsystem 60 allows a 1 G environment to be applied to a carousel 30—thus simulating the inertial acceleration conditions on earth (that is, 1 G or 1 times the acceleration of gravity). In addition, the device allows for the positioning of the egg holders 20 over the injection head 132 for embryo fixation. The egg turning subsystem 70 rotates the individual egg holders 20 for optimum incubation. As will be described below, the rotation of the egg holders 20 provides the closing mechanism (via egg holder bearing 22, described below) to seal the egg holders 20 during fixative injection (see FIG. 11).

Figure 5:
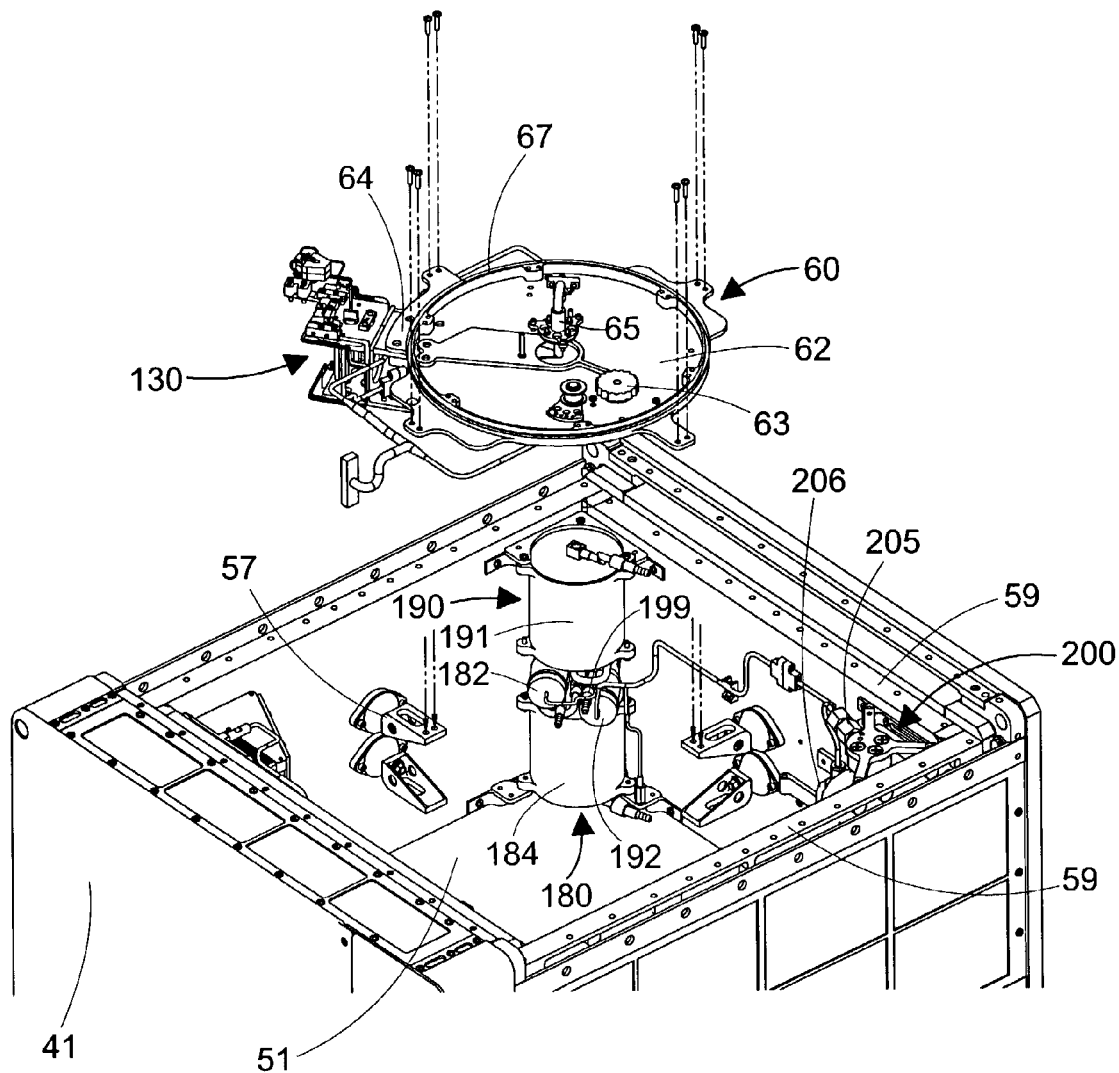
FIG. 5 is an isometric view of the centrifuge drive mechanism and its fittings in the interior of the inner housing of an embodiment of the invention.

The primary function of the carousel drive subsystem 60 shown in FIG. 5 is to provide a gravity-simulated 1-G environment for the egg samples 12. Based on the physical dimensions of the carousels 30, the carousel drive subsystem 60 rotates the carousels 30 at approximately 77 RPM in order to create this 1-G centripetal acceleration for the embryo specimens at the center of the egg holders 20. The egg holders 20 are positioned as far from the center of the centrifuge as geometrically possible within the inner housing 50 in order to minimize the required carousel 30 speed. In the preferred embodiment, the 77 RPM speed is achieved using a fifteen second ramp-up and ramp-down function in order to minimize disturbances to the egg samples 12.

A secondary function of the carousel drive subsystem 60 is the ability to index the egg holders 20 to an injection head 132 at an injection station 142 and then hold the carousel 30 stationary during this process. This is achieved by stopping the carousel 30 with a fifteen second ramp-down function and indexing the carousel 30 until two optical sensors 147 detect their respective home position indicators. The sensors 147 then "count" egg holder index markers 31 while the carousel drive subsystem 60 positions the proper egg holder 20 over the injection head 132. These reflective object sensors are both mounted to the injection head 132 (see FIG. 12). In order to maintain the low or microgravity environment for the stationary carousel 30, the indexing of the carousels 30 does not exceed a speed of 1 rpm. Once the carousel 30 has positioned the desired egg holder 20 over the injection station 142, the stepper motor 143 is placed in a hold mode to keep the carousel 30 from moving. Keeping the carousel 30 stationary is necessary for accurate engagement of the injection head 132 and the egg holder 20.

As briefly mentioned above, the device 10 achieves side-by-side control by containing two identical centrifuge systems 90 (that is, carousels 30 and their associated structures), each positioned as a mirror image to the other within the specimen volume 51. One of the carousels 30 is designated to rotate and create a centripetally accelerated control group of eggs. The other carousel 30 can remain stationary during incubation, creating a low gravity or microgravity experimental group. This arrangement allows the set of control eggs to experience the same environmental factors as the experimental group, such as launch and landing loads, oxygen and carbon dioxide levels, temperature fluctuations, and humidity levels.

Figure 6:
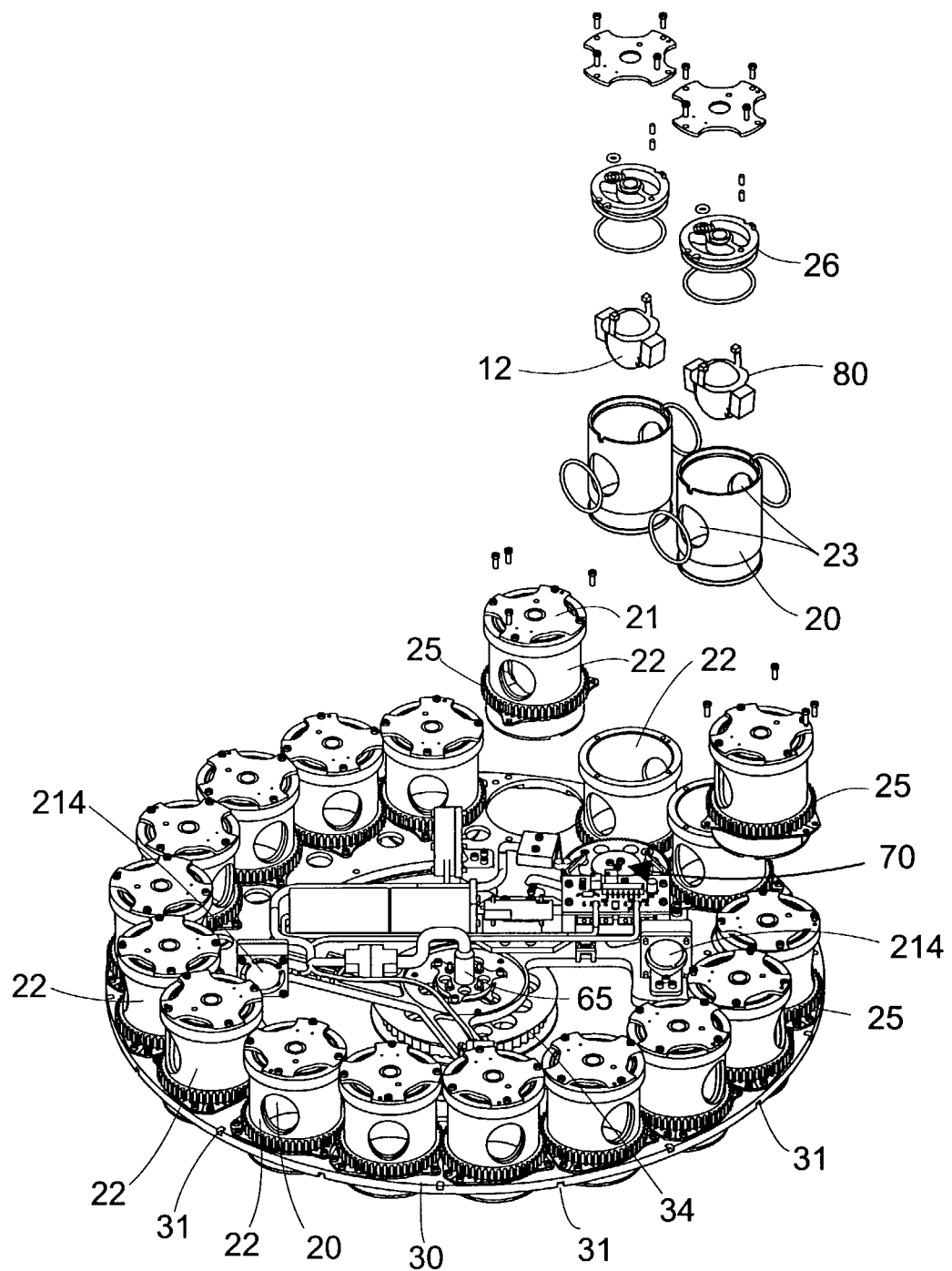
FIG. 6 is an isometric view of one of the centrifuges and the attached egg holders of a preferred embodiment of the present invention in which two egg holders are shown in exploded isometric view.

The carousel drive subsystem 60 is further divided into three components: the carousel plate 30, the carousel base 62, and the drive mechanism 63 (FIGS. 5 and 6). The carousel plate 30 is the main rotating component in the centrifuge system 90 (see FIG. 1 and FIG. 6). It provides mounting for the egg holders 20 and the egg turning subsystem 70. The carousel base 62 is the stationary component in the centrifuge which provides mounting location 64 for the injection system 130 and the primary structural support for the carousel plate 30. The drive mechanism 63 provides the torque required to rotate the carousel plate 30.

Referring generally to FIGS. 4-6, the carousel plate 30 provides structural support for the egg holders 20 and the egg turning subsystem 70. In space mission applications, it is designed to withstand the static and dynamic accelerations of launch and landing. The carousel plate 30 is the primary rotating component and is driven by the carousel drive mechanism 63. The preferred plate is manufactured from 0.200" thick 6061-T6 aluminum and is designed to minimize weight. In the preferred embodiment, the plate 30 comprises a hub portion 32 that sits atop a main drive gear 34, and an outer periphery that is connected by spokes 33 (FIG. 4).

In the preferred embodiment, the carousel plate 30 is coupled to the carousel base 62 at the hub portion 32 and the periphery. The hub portion 32 interfaces with the carousel base 62 through a slip ring 65 and main drive gear 34 (FIG. 6). The periphery of the carousel plate 30 is mounted to the carousel base 62 by a clamped bearing 67. The clamped bearing 67 configuration allows the carousel plate 30 to rotate while maintaining the required structural support for the carousel plate 30, while preventing wobble or out of plane rotation. Six outer bearing clips mount the carousel plate 30 to the outer race of the bearing. Six inner bearing clips mount the inner race of the bearing to the carousel base 62. These bearing clips are all manufactured from 6061-T6 aluminum and are mounted to the carousel and base via two #2-56 screws per bearing clip. The carousel plate/base interface is designed for quick assembly and disassembly, and minimizes weight where possible.

Referring still to FIGS. 4-6, the carousel plate 30 further provides support for the slip ring 65 and the main drive gear 34. The three spokes 33 transmit the torque of the drive mechanism 63 from the hub portion 32 to the periphery of the carousel plate 30 in order to turn the carousel 30. The spokes 33 also provide mounting for the egg turning gear motor 72 and a gear reduction mechanism. The carousel plate 30 provides the structural support for the egg holders 20 and also provides the interface point for the clamped bearing 67.

The clamped bearing 67 provides maximum planar stability of the centrifuge system 90 while withstanding any potential out of balance situations. The bearing 67 provides planar stability by supporting the carousel plate 30 at the farthest possible diameter from the center of the carousel plate 30. The four point contact bearing provides strength to withstand all radial, thrust, and moment loadings associated with launch, landing, and nominal operations. The bearing components 67, 69 are plated with Endurakote to prevent corrosion, decrease friction at the bearing, and increase the bearing life.

Figure 7:
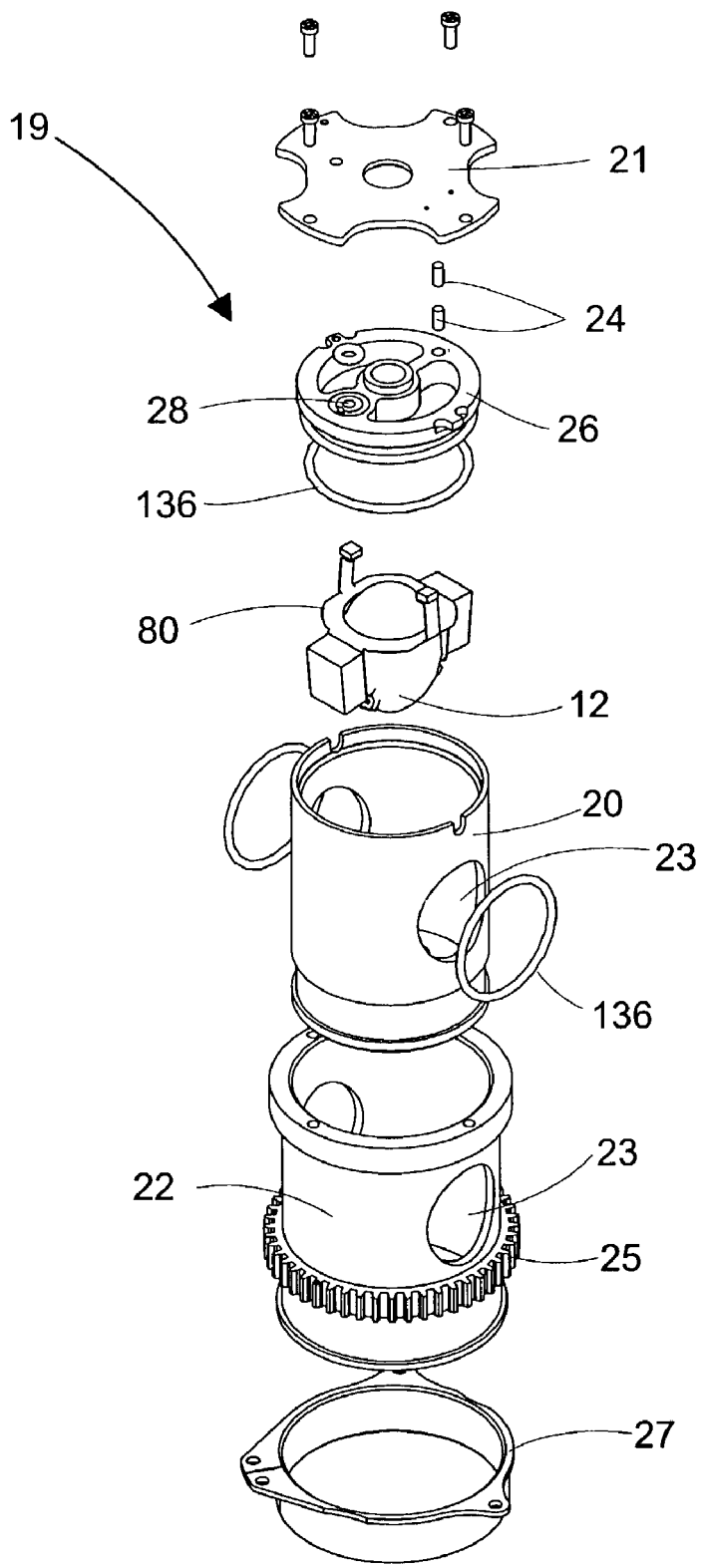
FIG. 7 is an exploded isometric view of one of the plurality of egg holders.

Referring to FIGS. 6 and 7, the egg samples 12 in the device 10 must be turned periodically in order to keep the yolk from settling to one side of the egg. Research has shown that turning the eggs increases hatch rates in commercial incubators. The egg turning also mimics the natural incubation process where the adult bird instinctively turns her eggs during incubation. The egg turning subsystem 70 is capable of periodically rotating the eggs in both the clockwise and counterclockwise directions. The egg turning subsystem 70 performs two primary functions: it turns the egg samples 12 during incubation to promote embryo development, and it also turns the egg holder bearing 22 to close the egg holder 20 during fixative injection.

To close the assembly before fixative can be injected, the egg holder bearing 22 and egg holder 20 must be turned relative to one another. The egg holder 20 has air holes 23 that allow air to circulate over the eggshell. Before the fixation process, the injection head 132 engages the egg holder 20 and locks it rigidly into place. The egg turning subsystem 70 activates and rotates the egg holder bearing 22 around the egg holder 20. This seals off the air holes 23 and makes the egg holder assembly a level of containment for the fixative. See FIG. 11 for more information on the injection system and injection process. See FIG. 7 for additional information on the egg holder assembly.

Typically, each carousel 30 has one egg turning subsystem 70. The egg turning subsystem 70 consists of a gear motor 72 that drives a series of gears by turning a spur gear on a lead egg holder 20 which, in turn, drives the spur gears 25 on both banks of the adjacent nine egg cups on each carousel plate 30. The gear motor 72 consists of a DC brushless motor coupled with a gearbox. This combination offers sufficient power and torque for continuous operation. Ideally, the gear train and motor 72 are designed for the worst case condition which occurs when the ninth or tenth egg holder assembly 19 must be closed. The gear motor 72 provides enough power to overcome the maximum required torque coupled with all inefficiencies at a rate sufficient to close an egg holder assembly in less than three minutes. The egg turning subsystem 70 preferably incorporates the use of a current limiting circuit. This circuit electrically limits the drive capability of the motor and prevents structural damage due to an obstruction or a seized specimen cup.

The preferred ADF device 10 contains thirty-six egg holder assemblies 19 within the specimen volume 51. Eighteen assemblies are mounted to each of two carousels 30. The egg holder assembly 19 operates on either a rotating or a stationary carousel 30. It interfaces with the carousel plate 30, the egg turning subsystem 70 and the injection system 130. FIG. 7 illustrates the egg holder assembly 19, which consists of several interdependent parts that may be grouped into four categories: (1) the egg isolator 80; (2) the egg holder 20 with endcap assemblies 26; (3) the egg holder bearing 22 with locking plate 133; and (4) the egg holder assembly bearing 27.

The egg holder assembly 19 serves two primary functions. First, it supports normal embryo development during an incubation mode. Second, it provides a sealed environment after embryo fixation and Level 1 containment for paraformaldehyde. Containment of paraformaldehyde is required for environmental reasons.

The egg holder assembly 19 provides all the interfaces with the egg sample 12. It restrains the egg sample 12 while allowing vital gas exchange of the embryo across the eggshell, and it provides the first level of vibration dampening for the egg sample 12. To promote normal embryo development, the egg holder assembly 19 provides a means to turn the eggs while the embryos are exposed to 1-G from the centrifuge system 90. As can be seen from FIG. 4, the turning means of the preferred embodiment comprises one or more gears that mesh with the gears located on the external surface of the egg holders 20. Power can be applied to the gears to impart a force on the external surface of the egg holder cups, thereby turning the cups and rotating the egg samples 12 therewithin.

Figure 11:
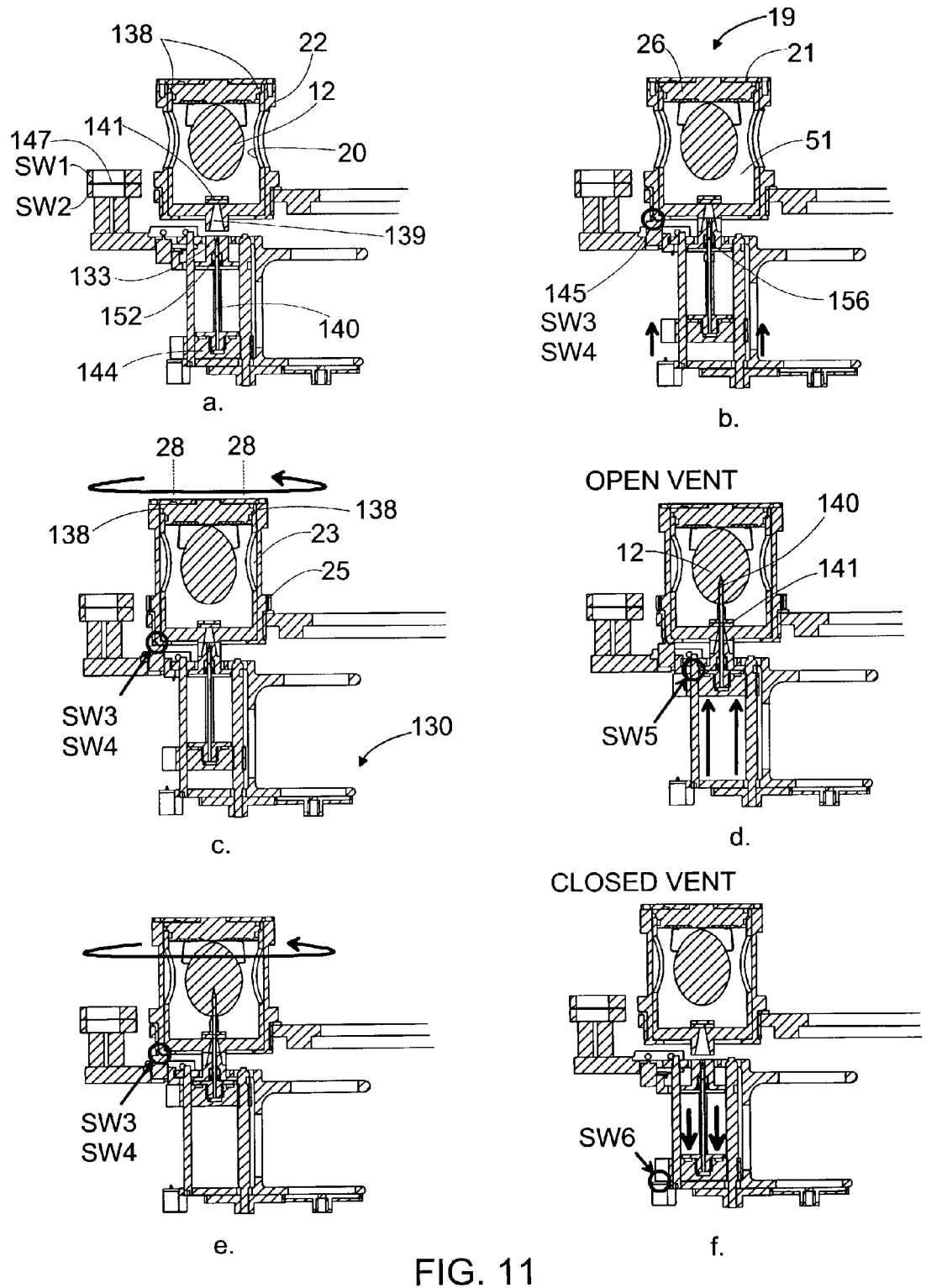
FIG. 11 is a functional diagram of the process of injecting one of a plurality of eggs using an injection system according to a preferred embodiment of the invention.

The egg holder assembly 19 provides the egg samples 12 with a sealed environment when the egg samples 12 are injected with fixative at predetermined times throughout the incubation period. FIG. 11 illustrates the process of closing the egg holders 20 during the injection process. The carousel plate 30 rotates until the desired egg holder assembly 19 is positioned over the injection system 130. The injection system locking plate 133, shown retracted in FIG. 11(a), is extended, holding the egg holder 20 stationary in FIG. 11(b). The egg turning subsystem 70 then rotates the egg holder bearing 22, FIG. 11(c), until the side air holes 23 are sealed and the endcap assembly 26 hydrophobic vent hole 28 (shown rotating in FIG. 11(c)) aligns with a corresponding hole in the locking plate. When such alignment occurs, this is referred to as the hydrophobic vent position, and gases are able to be vented out of specimen volume 51.

In the hydrophobic vent position a locking ball-and-spring 24 located between the endcap assembly 26 and the locking plate 21 prevents the egg holder bearing 22 from turning back to the open position (FIG. 11(b)). Locking plate 21 is preferably a metal disk or disk-like body above the endcap assembly 26 against which the egg holder bearing 22 rotates. The injection system 130 comprises a needle 140 that extends through a septum 141 in the egg holder assembly 19 and into the egg sample 12 as shown in FIG. 11(d). Then, a desired amount of liquid can be injected into the egg sample 12. In the preferred embodiment, 30 ml of fixative is injected. As the fixative fills the egg holder assembly 19, the hydrophobic vent 28 incorporated into the endcap assembly 26 vents the escaping air while preventing liquid from passing.

Upon completion of the liquid (fixative) injection, the egg holder bearing 22 is rotated and locked at the closed position, shown in FIG. 11(e), and cannot rotate in either direction. At the closed position, the egg holder assembly 19 provides a sealed environment to hold liquids and gases. In the closed position, the egg holder 20 is considered part of the first level of containment for paraformaldehyde, the preferred fixative.

Figure 8:
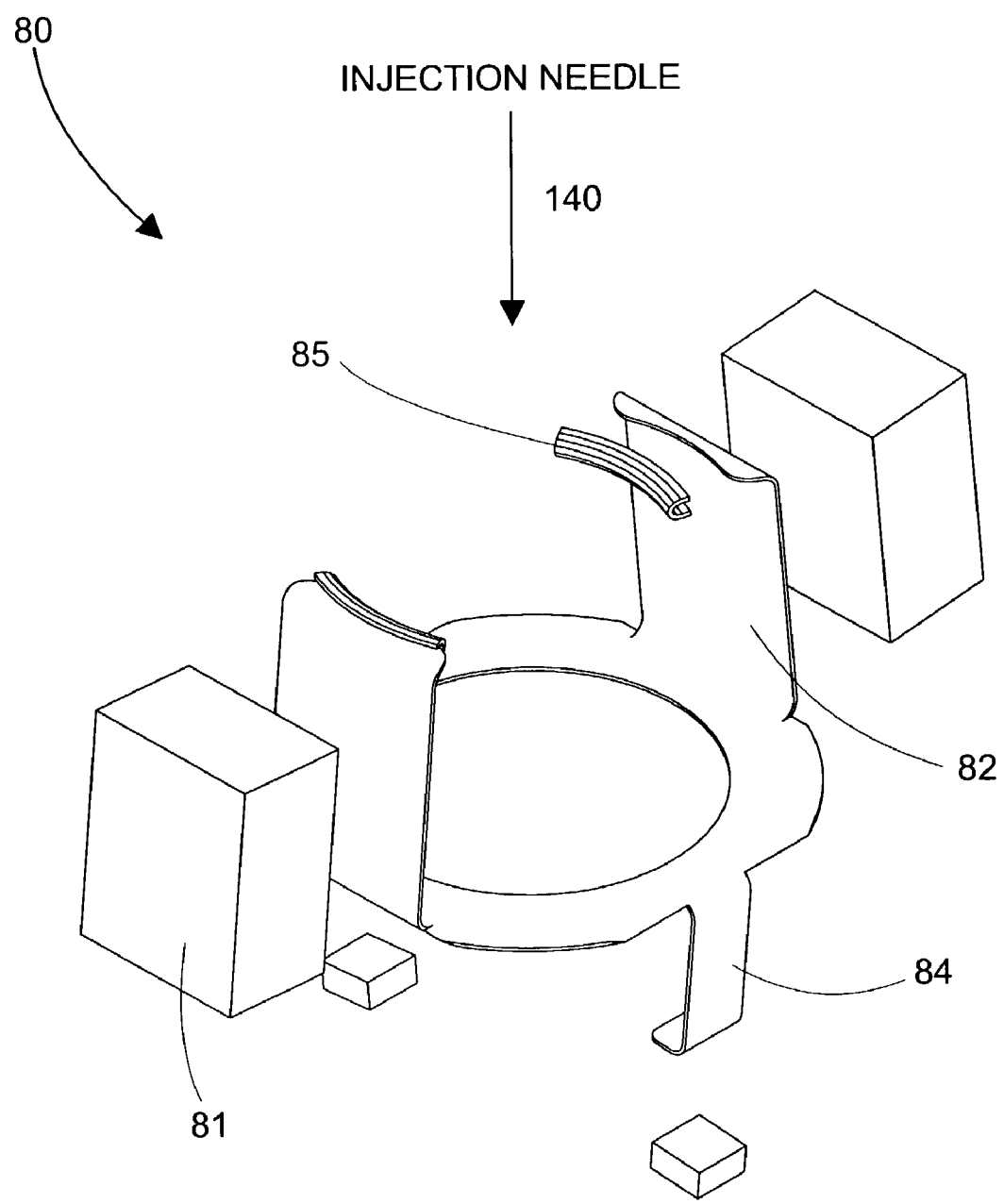
FIG. 8 is an exploded isometric view of one of the plurality of egg isolator assemblies.

FIG. 8 depicts the preferred embodiment of the egg isolator 80, shown inverted relative to FIG. 7 for clarity. The egg isolator 80 is the primary egg sample 12 (or specimen) interface. The egg isolator 80, generally, comprises two standoff legs 84 extending from one side of an annular ring, and two side arms 82 extending from the opposite side of the annular ring in a direction opposite the standoff legs 84. Preferably, the side arms 82 are resiliently opposed in a spring-like manner such that a force is needed to spread the free ends. Also, preferably, the sidearms 82 are located at a position on the annular ring that is offset from the position from which the standoff legs are located (see FIG. 8). Ideally, side arms 82 further comprise pads 85 (preferably of neoprene or similar material) attached to the inner egg-sample-engaging side thereof for engaging and holding egg samples 12. The egg isolator 80 serves two primary functions. First, it protects the egg sample 12 from gravitational loads and vibration forces throughout the mission. Second, the egg isolator 80 ensures that injection needle 140 penetrates the egg sample 12 during the injection process.

In the preferred embodiment, the egg isolator 80 is made from stainless steel and protects the egg samples 12 from gravitational pulls and vibration forces using small pieces of foam 81 (preferably F12 COHRlastic silicone rubber) attached to the side arms 82. The foam 81 is attached to the side arms 82 and standoff legs 84 of the egg isolator 80. The foam 81 interfaces with the inside walls of the egg holder 20 and the face of the endcap assembly 26 to hold the egg sample 12 firmly in place. The foam 81 also offers vibration damping at the specimen interface by minimizing vibration forces transmitted from the egg holder 20 to the egg isolator 80. The COHRlastic material is preferred due to its success in offgas testing and biocompatibility testing, and the fact that it is chemically resistant to paraformaldehyde, and offers good vibration dampening characteristics. The force exerted by the pads 85 on side arms 82 of the isolator is enough to hold the egg firmly in place without cracking the eggshell.

The egg isolator 80 holds the egg samples 12 firmly with standoff legs 84 to prevent it from moving with the needle 140 during the injection process, as the injection needle 140 is penetrating the large end of the egg 12. This ensures optimal position of egg sample 12 so fixative is injected at approximately the same area for each embryo.

Prior to placement in the egg isolators 80, the egg samples 12 are checked for cracks by candling, and are then screened by size and weight. This ensures cracked, oversized, or undersized eggs are discarded before installation.

Figure 9:
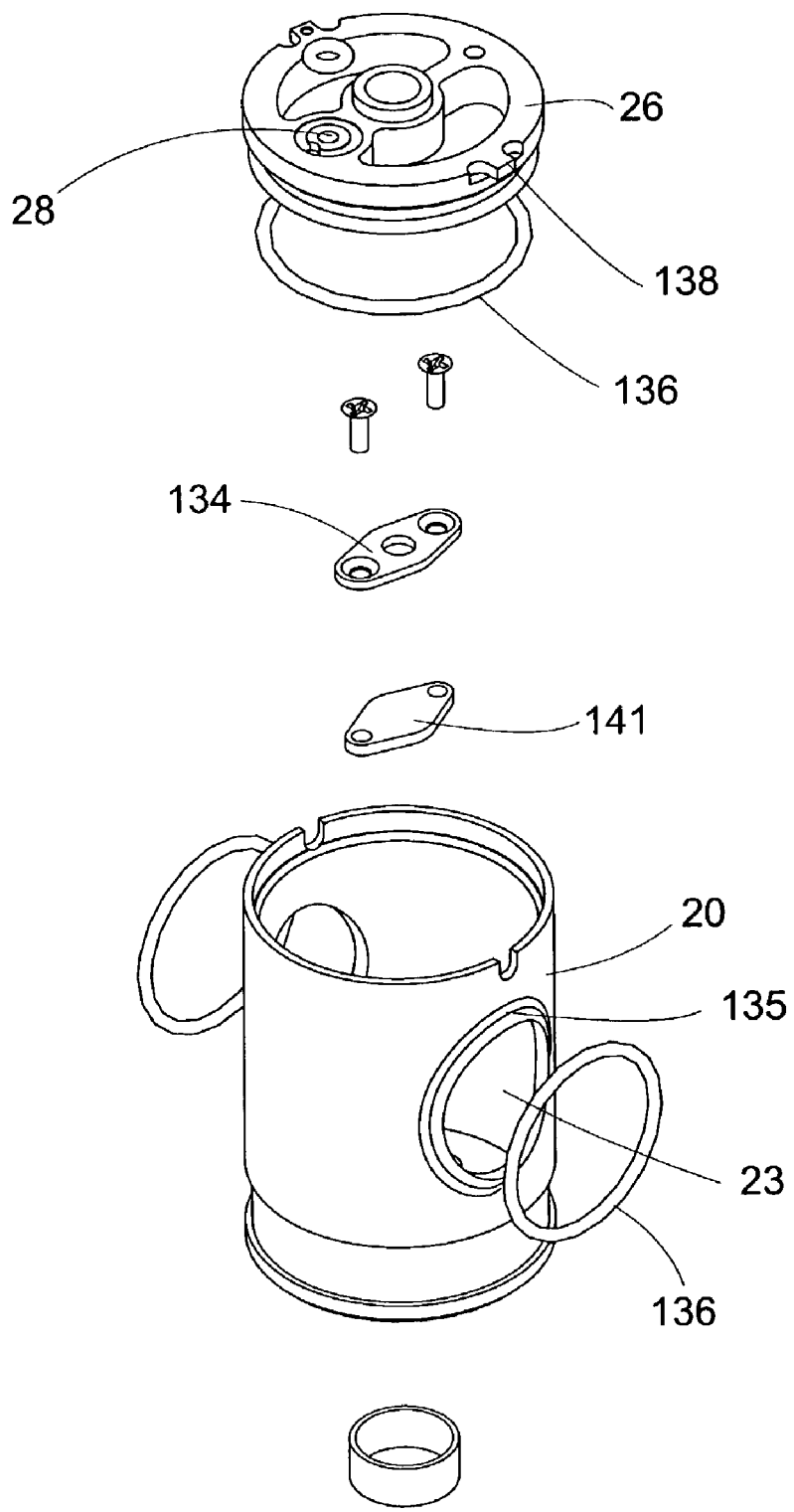
FIG. 9 is an exploded isometric view of one of the plurality of egg holders showing a septum for injection and a mechanical venting system.

Referring to FIG. 9, the egg holder cup assembly 19 with the endcap assembly 26 provides housing for the egg samples 12 and the egg isolator 80. The egg holder cup assembly 19 consists of the egg holder 20, septum 141, needle hole 152, septum mounting plate 134, and two flat head screws. The egg holder assembly 19 incorporates air holes 23 on each side to provide vital gas exchange of the embryo across the eggshell. Air holes 23 are encompassed by dovetail O-ring glands 135. The dovetail O-ring glands 135 are used to prevent the O-ring 136 from escaping the gland as the air hole opening 23 of the egg holder bearing 22 passes over it. Preferably, ethylene propylene O-rings 136 placed in the dovetail glands provide a sealed unit during and after the injection process.

Figure 10:
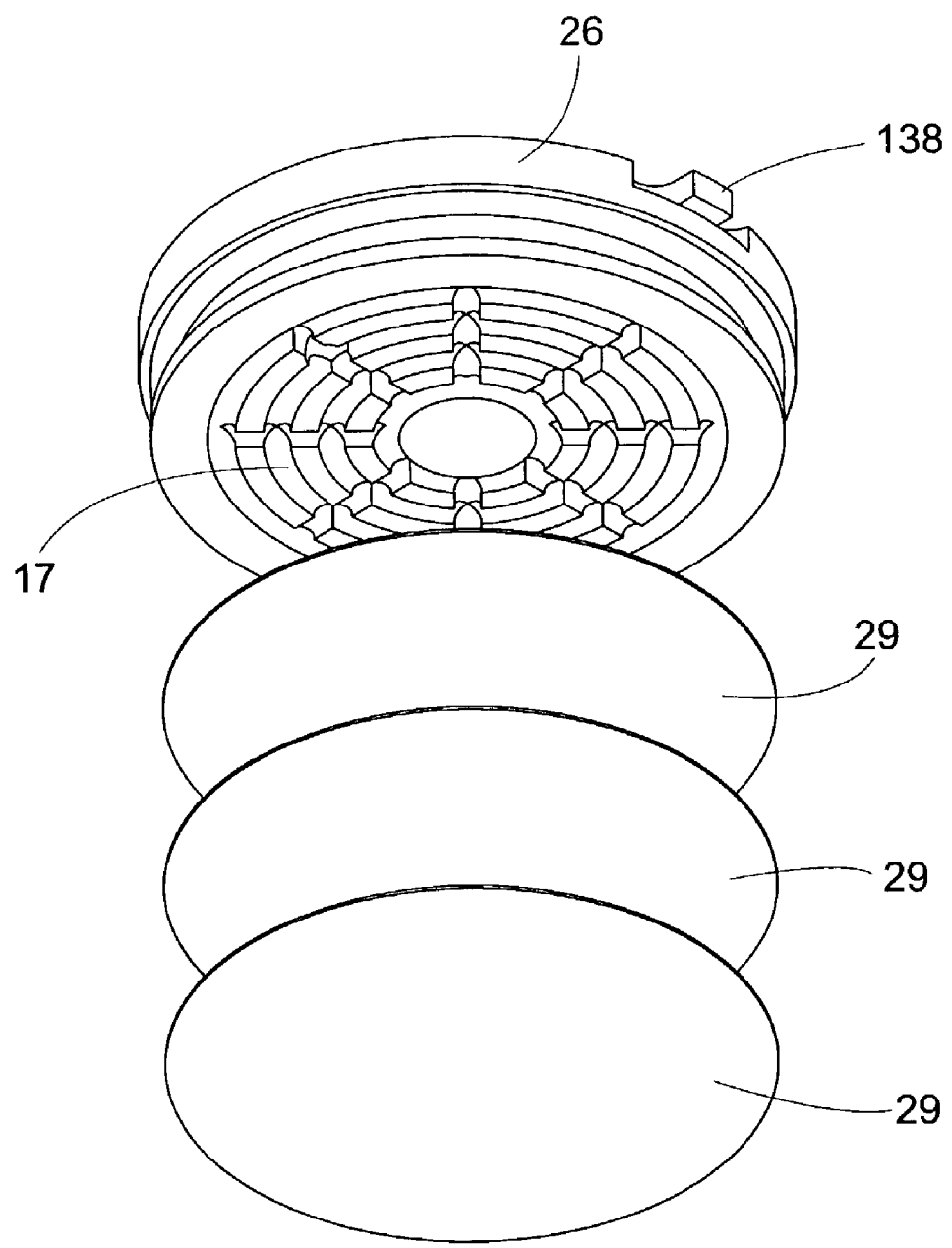
FIG. 10 is an exploded isometric view of one of the plurality of egg holder venting systems and filters.

The endcap assembly 26 interfaces with the egg holder assembly 20 to provide a vent 28 for the escaping air during the injection process while preventing liquid (paraformaldehyde in the preferred embodiment) from passing. FIGS. 7, 9, and 10 illustrate the endcap assembly 26. Endcap assembly 26 comprises (1) an Ultem 1000 endcap which further comprises, on its lower side, a disc with air channels machined therein; (2) two ethylene propylene O-rings 136; and (3) three layers of a Pall Corporation Poly Tetra Fluoro Ethylene (PTFE), 0.2 µm pore, hydrophobic membrane 29. Using three layers of hydrophobic membrane increases the burst pressure without significantly reducing the airflow. A silicone sealing cement (RTV) seals the membranes to the endcap. The preferred hydrophobic membrane 29 is compatible with paraformaldehyde and a wide range of chemicals, including aggressive solvents, acids, bases, and organic chemicals. The membrane prevents water intrusion pressure up to 90 psid. Asymmetric locking tabs 138 on the endcap assembly 26 fit into slots in the egg holder 20 preventing improper installation.

The locking plate 21 and the egg holder bearing 22 interface to provide a housing for the egg holder 20 and endcap assemblies 26. The egg holder bearing 22 provides a sealing surface for the air hole 23 O-rings 136, and plays an integral part in the egg turning subsystem 70. At the "hydrophobic vent" and "closed" positions, the inside diameter of the egg holder bearing 22 provides a sealing surface for the O-rings 136 located in the egg holder cup assembly 19.

As briefly stated above, the device 10 provides the ability to chemically "fix" each embryo, preserving the tissue for post-mission evaluation and providing a snapshot of the embryo development at a specific growth stage. The ADF device 10 provides a precise study of the embryo development in microgravity through chemical fixation of the specimen, which eliminates post-termination decay of the embryological tissue. The chemical fixation occurs through a controlled fixative injection process that centers around the operation of the injection system 130. The preferred injection system delivers 30 ml of 4% paraformaldehyde fixative to an embryo sample based on a pre-flight programmed timeline. The fixation preserves embryos prior to reentry.

Also as stated above, the egg holder cup assembly 19 interfaces with the injection system 130 for the delivery of fluid (fixative) to the embryo. FIGS. 11(a) and (b), for example, illustrate this interface. During the injection process, the carousel plate 30 positions the egg holder cup assembly locking tab 138 over the injection system locking plate 133 in FIG. 11(a). The injection system locking plate 133 extends into the egg holder cup locking tab 138, holding the egg holder cup assembly stationary (FIG. 11(b)). The egg turning subsystem 70 then rotates the egg holder bearing 22 to the hydrophobic vent open position (FIG. 11(c)). To allow for egg turning system gear backlash, the egg holder cup assembly 19 incorporates an "X" shaped slot into the locking tab 138. The "X" slot 139 design allows the injection system locking plate 133 to engage the egg holder locking tab regardless of whether the egg holder cup assembly 19 is rotated slightly off the injection position in either direction. To allow for tolerances in carousel plate 30 positioning, lead-in chamfers are incorporated into the locking tab. The chamfers allow the injection system locking plate 133 to engage the locking tab if carousel plate 30 rotation is slightly off the injection position.

Once the injection system locking plate 133 engages the egg holder locking tab 138, the needle 140 is extended into the egg holder 20 through the tapered lead-in hole 139 incorporated in the locking tab 138 (FIG. 11(d)). Fixative is then injected into the egg holder assembly. A septum 141 permits the needle 140 to pass into the egg sample 12, FIG. 11(d), and maintain a seal after the needle 140 is withdrawn. This process is analogous to multi-dose medication vials in which a hypodermic needle penetrates a septum to remove the pharmaceutical product, then reseals upon removal of the needle to form a leak-tight seal. However, the device 10 enables such a process to occur in low gravity environments where free fluid streams and two-phase flow is prohibited. A stainless steel plate (septum mounting plate 134) and two flat head screws retain the septum 141 in the egg holder cup assembly. The flathead screws maximize clearance between the end of the egg sample 12 and the septum plate 134.

The egg holder assembly 19 functions in three positions (FIG. 11). In the open position, the locking mechanism allows the egg holder bearing 22 to rotate toward the hydrophobic vent position, while preventing it from rotating in the other direction. This assures the egg holder cup assembly 19 aligns properly with the injection system locking plate 133 when the injection process is initiated. Before injection, the injection system locking plate 133 holds the egg holder cup assembly 19 stationary while the egg holder bearing 22 is rotated to the hydrophobic vent position. In the hydrophobic vent position, the locking mechanism ensures the egg holder bearing 22 will not rotate back to the open position. After fixative is injected, the egg holder bearing 22 is rotated to the closed position. In the closed position, the hydrophobic vent 28 seals, transforming the egg holder assembly 19 into a sealed container. The egg holder 22 bearing is prevented from rotating in either direction from the closed position.

Figure 12:
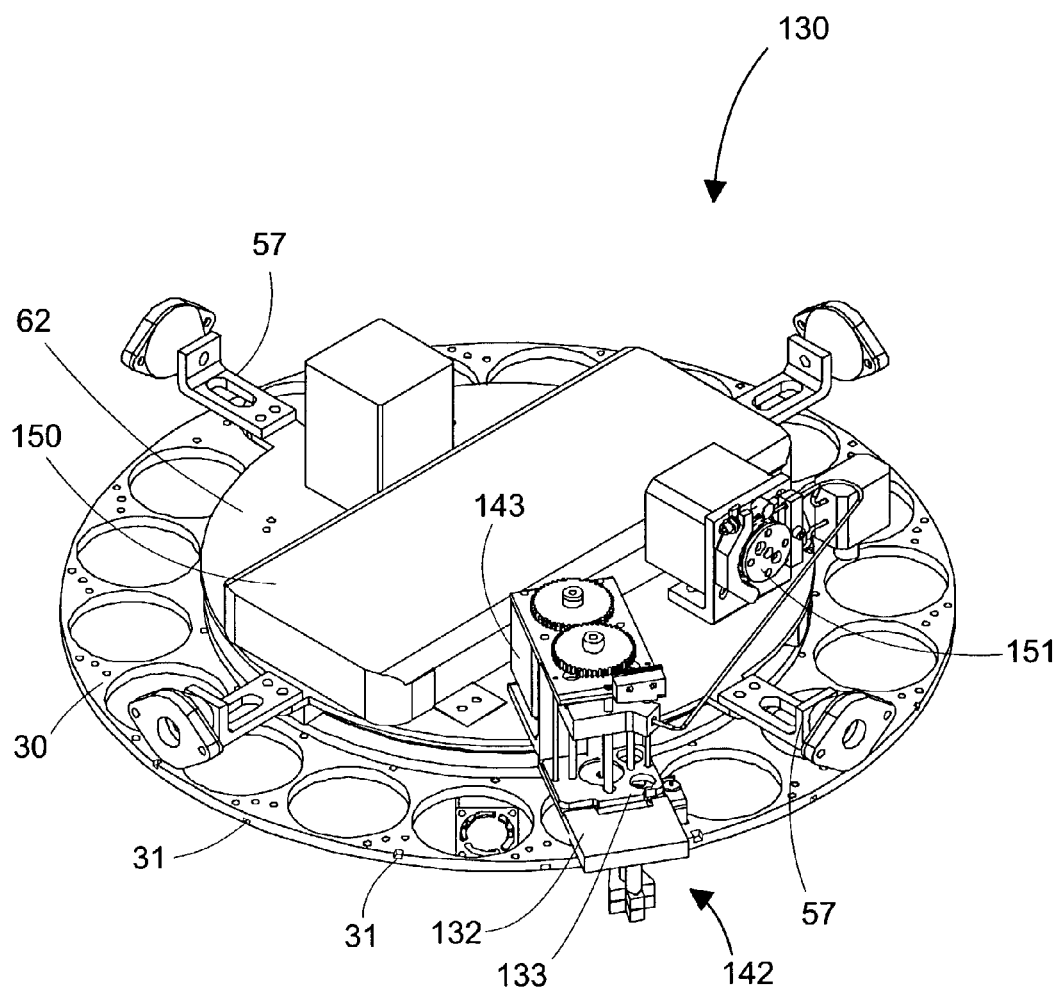
FIG. 12 is an isometric view of one of two assembled injection systems.

FIG. 12 shows the injection system 130. The injection system 130 has three major components: an injection reservoir 150, an injection pump 151, and the injection head 132. There are two complete and independent injection systems 130 in the ADF device 10. Each injection system 130 operates independently of the other. Each injection system 130 is also mounted independently of the other. Each system is located on the bottom side of one of the carousel bases 62 (see FIGS. 1 and 5 for details on the centrifuge system 90). This provides a complete injection system 130 for each centrifuge unit which increases the reliability of the ADF science, as well as prevents any unnecessary interaction between the test and control groups of egg samples 12.

The initial storage of the liquid (again, in the preferred embodiment, it is 4% paraformaldehyde) occurs at the injection reservoir 150 (see FIG. 12). The injection reservoir 150 contains the fixative solution in a bag surrounded by an aluminum container 153. The aluminum container 153 protects the bag from puncture and restrains the bag. The aluminum container 153 is designed to be as lightweight as possible, while still providing protection for the bag. Preferably, it is made from a machined piece of 6061-T6 aluminum and mounts to the center of the carousel base 62 using eight #4-40 fasteners with washers. In the preferred embodiment, each reservoir bag is sized to contain enough fixative for eighteen egg samples 12 to be immersed in 30 ml (0.54 L) of paraformaldehyde. The reservoir bag of the preferred embodiment is manufactured by the American Fluoroseal Corporation (AFC).

A pump 151 provides the means by which the fixative flows in the injection system 130. The fixative pump 151 is preferably a peristaltic pump built by Space Hardware Optimization Technology, Inc. ("SHOT, Inc."). The peristaltic pump 151 provides minimal deviation in output volume independent of small deviations in head pressure. An Oriental Motors PK243-03AA stepping motor provides a precise, repeatable, programmable control of the peristaltic pump. Controlling the speed and number of steps of the pump motor varies the flow rate of paraformaldehyde, the quantity pumped, and the pressure in the injection system 130. Tests with the pump 151 have shown that it is capable of a controlled, variable flow rate of 0 to 29.0 ml/min, based on the speed of the motor. The pump 151 mounts to the bottom of the carousel base 62 using four #4-40 fasteners.

The main component of the injection system is the injection head 132. The injection head 132 extends a needle 140 into the egg holder 20 and assists in the closing of the egg holder 20. The injection head assembly consists of an Oriental stepper motor that drives a lead screw. The lead screw translates a needle carrier 144 and locking plate to engage the needle 140 with the egg holder 20. The locking plate 133 contains 2 O-rings that are located on either side of the needle hole 152 when the needle 140 is fully retracted, providing a contained environment for the needle outlet when retracted. The injection head 132 and bracket also serve as mounting structures for several of the carousel drive and injection process switches.

A plurality of switches are used to control the operation of the injection system 130, though more or fewer than those described herein may be utilized, depending upon the application for the device 10 and the types of testing and manipulation of the samples required. Each injection system 130 has an independent set of identical switches. These switches are used by software to determine if the egg holder assemblies 19 and the carousel 30 are in proper position before fixative delivery is allowed to occur. In the preferred embodiment described herein, these switches are microswitches driven by optical sensors located at various positions in the assembly. It will be appreciated, however, that other types of switches could be employed in the device 10. For instance, micro-switches could be used to detect detents located at various positions. In addition, magnetic switches could be employed by placing small permanent magnets in the plate and a sensing coil where the current optical switches are located. The optical switches described herein are preferred due to their simplicity and reliability.

Optical switches (designate with "SW") mounted to the injection head 132 are used to detect carousel 30 rotation position. The egg holders 20 can either close in the clockwise or counterclockwise direction. SW1 and SW2 allow the software to sense the proper direction for closing. Cup 1 is considered the "home position" of the carousel 30. Both SW1 and SW2 will be active (logic "1") at home position. When cups 2 to 18 are aligned, SW1 or SW2 will be active, depending upon the direction needed for closing. The optical switches are also used as a tachometer for the carousel 30 rotation speed. By using SW1, the software will detect ten pulses per revolution of the carousel. In addition, sealed mechanical switches 145 are used for injection and egg rotation positions.

When a sample needs to be fixed, the carousel 30 must be positioned to locate the sample 12 directly over the injection head 132. This positioning is done in two steps. First, the centrifuge stops and optical switches SW1 and SW2 locate reference markers at the home position on the carousel. SW1 and SW2 count the index markers 31 or "tick marks" located adjacent to each egg holder 20 as the carousel 30 rotates. When the carousel 30 reaches the "tick mark" 31 corresponding to the desired sample, the carousel 30 stops and locks into position. The injection process is now ready to begin. FIG. 11 illustrates the injection process.

After the desired sample has been aligned over the injection head 132 (FIG. 11(a)), the stepping motor 143 drives the lead screw, which in turn drives the needle carrier 144 toward the egg holder 20. The locking plate 133 travels concurrently with the needle carrier 144 during its first stage of travel. Switches SW3 and SW4 contact the bottom of the egg holder bearing 22. Once the switches have actuated, the needle 140 travel stops. At the end of the first stage of travel, the locking plate 133 has fully engaged the egg holder (FIG. 11(b)).

The egg turning motor 72 on the carousel then rotates the egg holder bearing 22 to close the egg holder 20. The turning process exposes the hydrophobic membrane 29 while the injection head 132 holds the egg holder 20 stationary. The needle 140, which is still fully enclosed by the two O-rings, has not yet penetrated the septum 141 on the egg holder 20. When the egg holder bearing 22 reaches the hydrophobic position, a cutout in the egg holder bearing 22 causes SW3 to disengage. The egg turning motor 72 stops. The egg holder 20 is now in "hydrophobic position" (FIG. 11(c)) and the egg holder 20 is ready to receive paraformaldehyde.

Next, the injection head 132 indexes the injection needle 140 up out of the locking plate shroud, through the egg holder septum 141, and into the egg sample 12 (FIG. 11(d)). Switch SW6 indicates needle engagement by actuating against the needle carrier 144 when the injection needle 140 is fully extended. The pump 151 activates, delivering 30 ml of paraformaldehyde to the egg holder 20.

Once the pump 151 has completed, the egg turning motor 72 activates again, turning the egg holder bearing 22 to close the hydrophobic membrane 29 (FIG. 11(e)). The egg holder 20 is now in the "closed" position and is now a sealed component. The closed position is indicated by switch SW4, which disengages into a cutout in the egg holder bearing 22 once the cup is fully closed.

Once the egg holder 20 is in the closed position, the injection head 132 retracts the needle 140 into the locking plate 133 and retracts the locking plate 133 from the egg holder 20 (FIG. 11(D)). As the needle 140 retracts, the needle hole 152 returns to the sealed position between the two O-rings 156 in the locking plate 133. Switch SW6 indicates when the needle 140 and locking plate 133 have been fully retracted. The carousel 30 is now free to rotate. The full injection process can be programmed to last virtually any duration. However, in the preferred embodiment for space missions, this process will take a maximum of ten minutes; furthermore, no two egg samples 12 will be fixed closer than ten minutes apart. This is a result of a combination of space flight power requirements (typically, 130 W max.) and the time needed to accurately place the injectors under the desired egg holder 20.

The ADF device 10 of the preferred embodiment further includes several systems that control and regulate the atmosphere in and around the egg samples 12. For an embryo to develop normally into a fully developed chick, the egg water content must evaporate at a controlled rate. When the egg contents dry too rapidly, the chick is smaller than normal. Similarly, when the contents evaporate too slowly; the chick is larger than normal. In either case, the embryo is weakened, resulting in lower hatchability and a chick of poor health and reduced scientific value. To ensure proper dehydration of the egg contents, studies have shown the relative humidity of the air during the first sixteen days should be maintained at approximately 65% RH. To regulate the evaporation of the egg contents, the amount of moisture in the surrounding air must be controlled.

FIG. 1 further depicts a humidity control system comprising two different subsystems. A moisture delivery system 170 supplies additional moisture when the humidity level in the hardware becomes low. In contrast, an automated moisture removal system 180 removes excessive moisture when the humidity inside the specimen volume 51 becomes too high. These two subsystems are designed to work together to maintain the proper humidity level inside the ADF device 10.

The moisture delivery system 170 (FIG. 1) adds a precise amount of water to the air within the controlled volume of ADF device 10. The moisture delivery system 170 is activated whenever a relative humidity sensor 172 reads a value that is below a lower limit humidity set point 174. In the preferred embodiment, the moisture delivery system 170 consists of a Teflon reservoir bag connected, using flexible silicone tubing 176, to a solenoid diaphragm pump 177. The pump 177 dispenses water directly into a sponge 178 (not shown) with each activation. The maximum activation rate is two hertz.

As stated, the ADF device 10 also has the ability to remove water vapor from inside the specimen volume. The moisture removal system 180 activates when the humidity level (FIG. 14) inside the specimen volume 51 increases above an upper humidity set point 175, which typically ranges from approximately 50% to 75% relative humidity. Obviously, however, other levels of humidity can be employed so as to maintain the specimen volume 51 at the desired humidity level.

FIG. 5 shows a layout including the moisture removal system 180. This system mounts in the back corner of the specimen volume 51. The moisture removal system 180 consists of a desiccant canister 184, diaphragm air pump 182, O-rings, and cover plate with mounting brackets.

When the relative humidity exceeds the upper humidity set point 175 (50 to 75%), a diaphragm air pump 182 is activated. Air within the specimen volume 51 is pulled into the diaphragm air pump 182. The air is pumped into the desiccant canister 184, which preferably is a sealed aluminum (6061-T6) canister. After leaving the exit end of the canister 184, the air is blown through a nylon check valve with a crack pressure of 0.09 psig back into the specimen volume 51.

The desiccant canister 184 of the preferred embodiment is 3.0 inches long, with a 2.5 inch ID and 0.040 inch wall thickness that can hold up to 95 grams of silica gel desiccant. The desiccant selected for device 10 is a multiform silica gel desiccant, which has an absorption capacity of 0.35 gm $H_2O$/gm desiccant at a 40° C. operating temperature.

The ADF device 10 of the preferred embodiment also has the ability to regulate the atmosphere within the specimen volume 51. Permeation of oxygen ($O_2$) and carbon dioxide ($CO_2$) through the eggshell is vital to the developing embryo. In an enclosed environment, there is a need for oxygen replenishment in order to maintain proper oxygen levels. Similarly, there is a need for maintaining the level of carbon dioxide below about 0.5% since higher levels have been found to inhibit metabolism of the developing embryos. Maintaining suitable concentrations of oxygen and carbon dioxide in the ADF specimen volume 51 is therefore critical to support normal embryo development. As a result, the ADF device 10 further comprises a gas monitor and control system comprising a carbon dioxide system 190 and an air system 200. These systems ensure the environmental parameters with the ADF device 10 remain within acceptable limits.

Referring generally to FIG. 5, the air system 200 and $CO_2$ system 190 each serve at least two functions: sensing and control. Sensors 202 and 193 read $O_2$ and $CO_2$ levels, respectively, within the ADF device 10 and send the data to a DMS computer 120. When the DMS computer 120 receives an "out of range" signal, it initiates the proper response from the appropriate system. The air system 200 controls the $O_2$ level within the specimen volume 51 by opening a 2-way solenoid valve briefly, pulsing air into the specimen volume 51. Conversely, the carbon dioxide system 190 removes $CO_2$ by pumping air through LiOH, as will be described below.

Permeation of oxygen through the eggshell is vital to the developing embryo. The ADF device 10 carries its own supply of air inside an air tank 201 capable of holding 5,000 psig. The air within air tank 201 is comprised of 30% oxygen and 70% nitrogen. The air system 200 allows control of the level of $O_2$ independent of cabin air concentration. The air system 200 activates when the $O_2$ partial pressure or oxygen concentration level 204 inside the specimen volume 51 becomes less than 21% of atmospheric pressure (14.7 psi), or 3.087 psi. This allows the addition of $O_2$ to the specimen environment. The air system 200 consists of an air tank 201, a cap, a flow-limiting orifice 205, seamless stainless steel tubing, and a solenoid valve 206.

The $O_2$ level is monitored with a medical oxygen sensor 202. When the partial pressure 204 drops below 3.087 psi (21% of 14.7 psi), the DMS computer 120 sends a signal to activate the 2-way solenoid valve 206. After a single pulse, the system pauses momentarily to allow the oxygen to mix within the existing air within the specimen volume 51.

In the preferred embodiment, the 2.66 inch outer diameter×8 inch long canister is capable of holding 5,000 psig at 50° C. with an air volume of 140.5 liters when allowed to expand to 1 atm. However, the tank is only filled to 3000 psig. This allows pressure to increase within the tank, due to a temperature increase, without exceeding the maximum differential pressure (MDP) for the tank.

In the preferred embodiment, the air system 200 maintains optimal oxygen levels within the ADF device 10 by supplying air (30% $O_2$ and 70% $N_2$) when the oxygen concentration 204 falls below 3.087 psi (21% of 14.7 psi) within the specimen volume 51. The $CO_2$ system 190 maintains optimal carbon dioxide levels by removing carbon dioxide from the system when the concentration level 194 rises above 0.0735 psi (0.5% of 14.7 psi) within the specimen volume 51. Obviously, these levels can be altered depending on the specific applications employed.

As stated above, maintaining the appropriate carbon dioxide levels in the specimen volume is also critical to normal embryo development. The carbon dioxide system 190 activates when the $CO_2$ partial pressure inside the specimen volume increase above 0.0735 psi (0.5% of 14.7 psi) removing $CO_2$ from the environment.

FIG. 5 shows the $CO_2$ removal system 190 and the humidity removal system 180. The two systems are mounted together into a back corner of the specimen volume 51. The carbon dioxide system 190 consists of the LiOH canister 191, diaphragm pump 192, O-rings, and cover plate with mounting brackets.

The LiOH canister 191 of the preferred embodiment is approximately 3.0 inches long, with a 2.5 inch ID and 0.040 inch wall thickness. The canister 191 preferably can contain up to 55 grams of LiOH, which converts $CO_2$ in the air into solid $LiCO_3$ and $H_2O$. The air is then blown through a check valve 199 to prevent leakage and backflow with a crack pressure of 0.09 psig back into the ADF specimen volume 51.

For a typical 13-day space mission, the ADF device 10 needs 38 grams of LiOH to adequately scrub $CO_2$ from the specimen volume 51 containing thirty-six Japanese quail egg samples 12. The amount of LiOH required drops significantly when the injection system 130 is used to preserve eggs at various times during the 13 day experiment duration.

In the preferred embodiment, there are two significant ADF thermal modes of operation, a chill mode and an incubation mode. A typical flight would consist of ADF device 10 being loaded with egg samples 12 on the ground and put in a "hibernation" cooling mode to keep the eggs cool enough to suspend development and minimize the impact of launch variables on embryo growth. The ADF device 10 is loaded into the Shuttle Middeck while powered and remains active in the chill mode throughout the Shuttle launch. During egg incubation, ADF is in a heating mode to promote egg development. When in incubation mode, ADF activates several subsystems that change the heat dissipation compared to the chill mode, such as rotating the egg carousel.

The primary objective of the thermal design is to efficiently transfer the heat dissipated by the eggs and other electrical components to the surrounding environment without exceeding specified thermal limits. There are two avenues for heat to enter or escape the ADF device 10: one avenue is through the front panel cabin air fan 210; the other is through the sidewalls via conduction and radiation. The ADF device 10 is designed to use the cabin air for its primary cooling source.

Referring again generally to FIG. 2, in the preferred embodiment the front panel 41 comprises two panels: electronics panel 46 and electronics access panel 47. Each is manufactured from 5/8" 6061 aluminum plate. The electronics panel mounts to the electronics housing frame 220. All of the power and data connectors, push buttons, and the LCD screen mount to the electronics panel. The electronics access panel mounts to the electronics housing frame 220. It overlaps and mounts to the electronics panel. It provides containment and protection for the electronics boards 122; heat exchangers 212, 217; and air baffles. The electronics access panel contains openings 216, 219 that allow airflow for the heat exchangers. The front door is designed to withstand kick-off loads.

Figure 13:
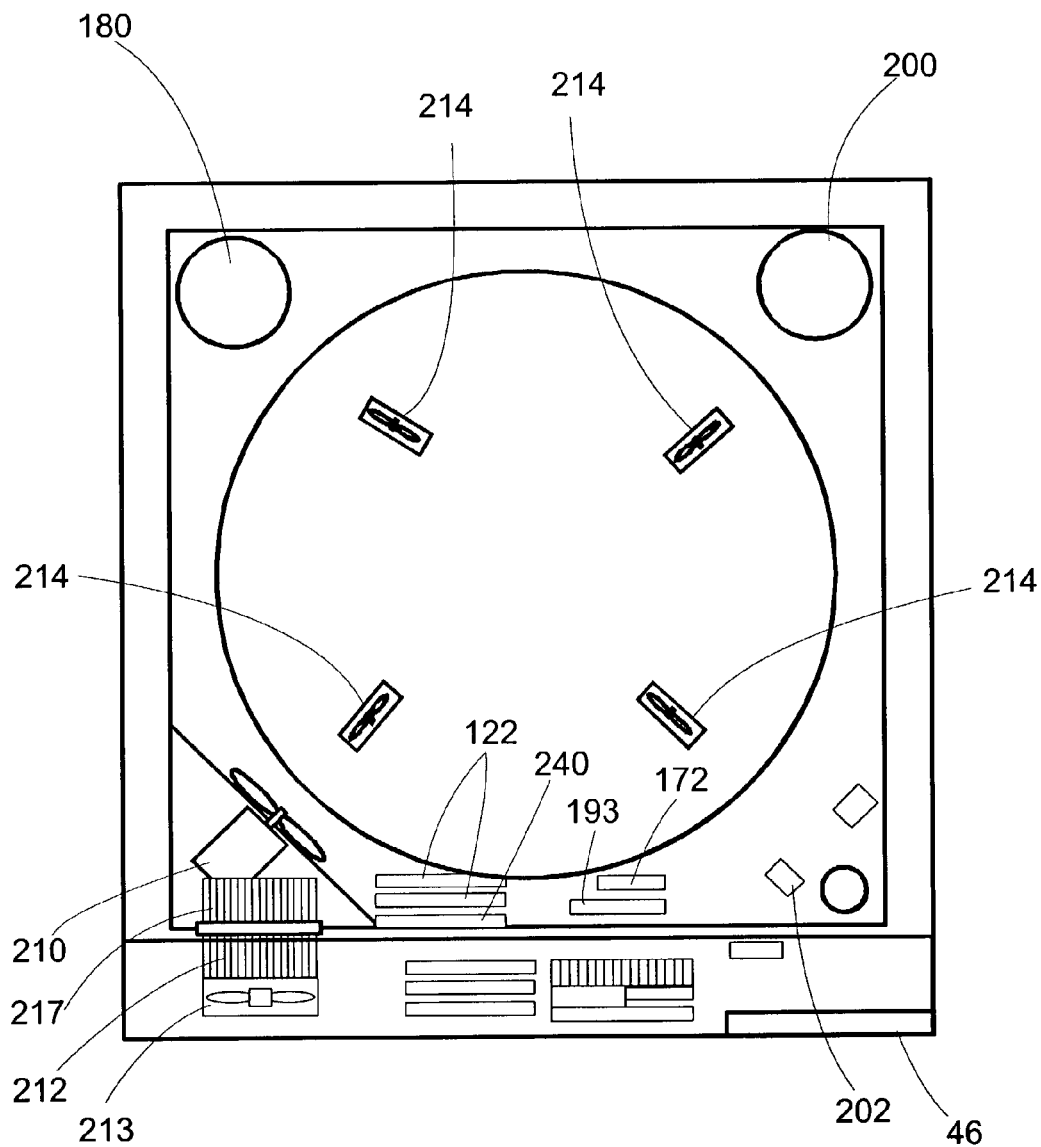
FIG. 13 is a diagram of the internal environmental control system.

FIG. 13 shows a schematic of the environmental control systems. An inner air circulation loop circulates air from the inner ThermoElectric Device (TED) heat sink (heat exchanger 212) to the other specimen volume subsystems and across the individual egg holders 20 by way of front panel cabin air fan 210. Each egg holding carousel 30 contains four small 25 mm square fans 214. Fans 214 assist in making the inner air circulation loop homogeneous. Each small fan 214 is rated for 1.3 CFM at zero flow resistance. FIG. 13 schematically shows the relative locations of the internal fans 214 within ADF.

An outer air circulation loop draws air from the crew cabin and pushes it through the external heat sink 212 and over the supporting electronics 122. The outer air circulation loop is powered by two fans 213. Each fan 213 draws air directly from the crew cabin via the front panels left side air vent 216 and blows over one external TED 217. The external heat sinks are arranged so the cabin air is drawn into the electronic bay on the left (as shown in FIG. 13) and blows towards the electronics 122 mounted in the center of the front panel. After the air cools the electronics, the air is returned to the cabin via a second exhaust screen opening 219 on the right side of front panel 41.

In the preferred embodiment, data management and control of ADF device 10 is accomplished by a network of microcontrollers instructed by a 486-based CPU 120. The CPU is a PC104 architecture. The PC104 architecture is used for embedded controller applications. PC104 is based on the ISA standard for desktop PC's. Its similarity to desktop standards results in more efficient software development and testing.

The CPU communicates with the microcontrollers via a two-wire interface protocol known as "Controller Area Network" (CAN). CAN was originally designed as a rugged interface for the automobile industry. Its purpose is to reduce interconnects by distributing the processing to microcontrollers, and providing a method to overcome communication interruptions and upsets. The CAN protocol ensures that interrupted data streams are re-transmitted and conflicts cannot occur between multiple nodes (microcontrollers).

The CPU is equipped with 40 MB of FLASH-based, non-volatile memory. The memory is used for program space and data storage. The design includes a PC104 Ethernet card used for development and testing. The card remains in the ADF device 10 for flight for final checkout testing.

Figure 14:
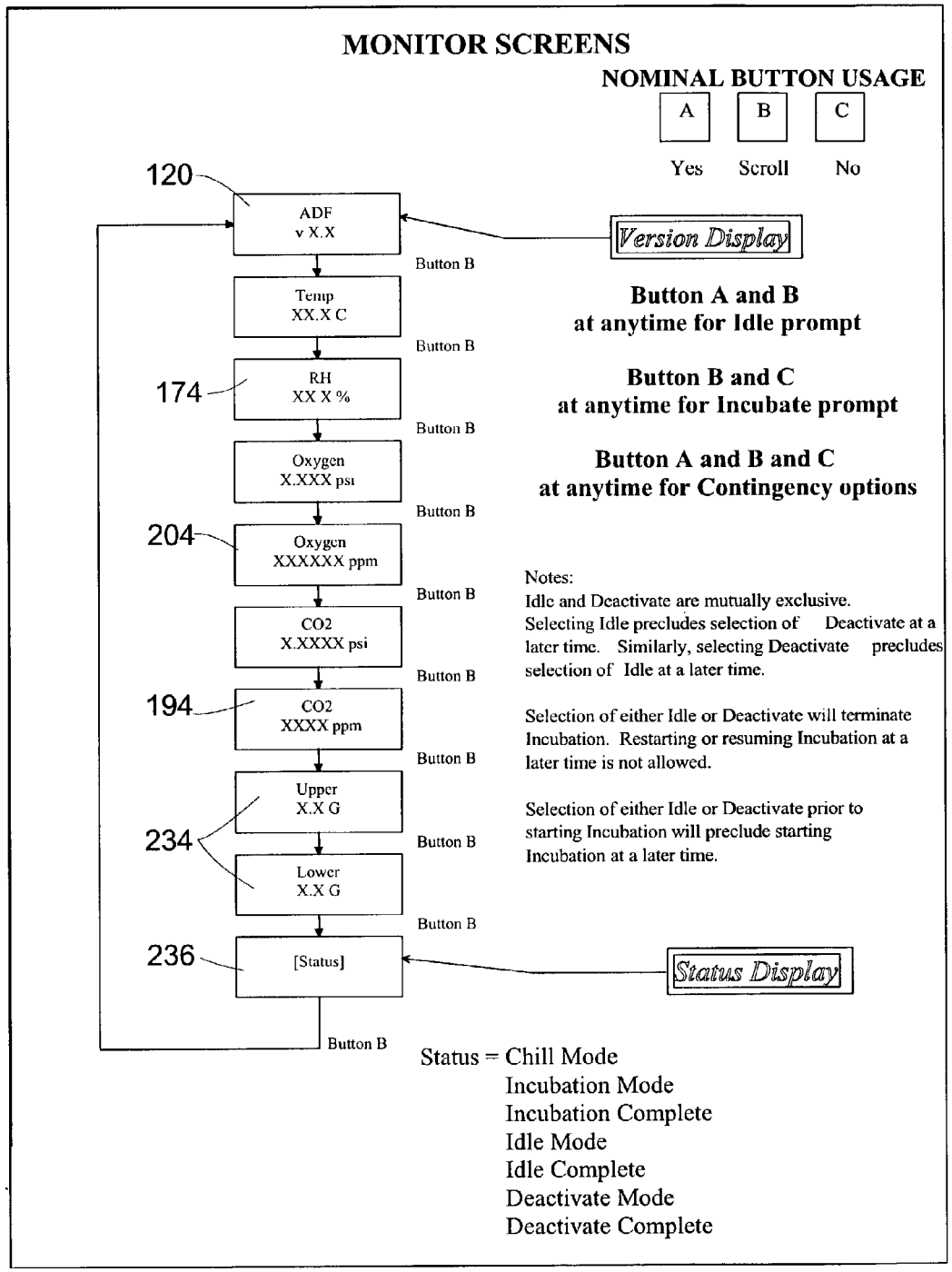
FIG. 14 is diagram depicting simultaneously the various display screens available to a user of the algorithmic control programs for operating the mechanics and maintaining the internal environment of the invention.

For ease of use, the user 100 can perform tasks with three pushbuttons, guided by menus and instructions on an LCD display. FIG. 14 is a diagram showing all the display screens a user will see at various times during operation of the user panel for the ADF device 10. Each rectangle shown in FIG. 14 represents a separate screen that will be displayed on the main screen. The Main Screen is the start point for using the LCD functions. From the Main Screen, the user can scroll to subsequent displays by pressing Button B. The subsequent screens display the specimen environment atmospheric temperature, oxygen level 204, carbon dioxide level 194, relative humidity, artificial gravity level 234 for each carousel 30, and experiment timeline status 236. The display showing the timeline status 236 is also referred to as the Timeline Screen. This screen indicates the current status of the experiment timeline: idle, active, or finished. From the Timeline Screen 236, pressing Button B to scroll to the next display returns to the Main Screen.

The user advances to a shutdown prompt at any time by pressing Button A and Button C simultaneously. At the shutdown prompt, Button A allows for shutdown and Button C returns to the Main Screen. If no selection is made, the display returns to the Main Screen.

As described above, the ADF device 10 contains 1.1 L of 4% paraformaldehyde for embryo fixation. Paraformaldehyde is a level 2 hazard, requiring 3 levels of containment on space vehicles. The first level of containment is the injection system 130. This includes all lines, fittings, reservoirs, and so forth. After an egg sample 12 is injected, the egg cup holder 20 also becomes a part of the first level of containment. The second and third level of containment are provided by the inner housing 50. A vent system 52 is incorporated in the inner housing 50 to allow venting of the specimen volume 51 while still providing required containment of hazardous materials. In the preferred embodiment for space-flight experimentation on developing bird embryos, the ADF device 10 contains the following hazardous chemicals: water (level 0); 4% paraformaldehyde (level 2); LiOH (level 2); and silica gel desiccant (level 0). The first level of containment is provided by the corresponding subsystem described above. The remaining two levels of containment are supplied by the inner housing 50 and the vent system 52.

As described, the ADF device 10 supplies oxygen for the developing embryos in the form of air with 30% $O_2$ and 70% $N_2$. Since the specimen volume 51 is not a pressure vessel, it must vent the pressure introduced by the air system when air is supplied to the embryos while still maintaining two containment levels of the hazardous materials.

Figure 16:
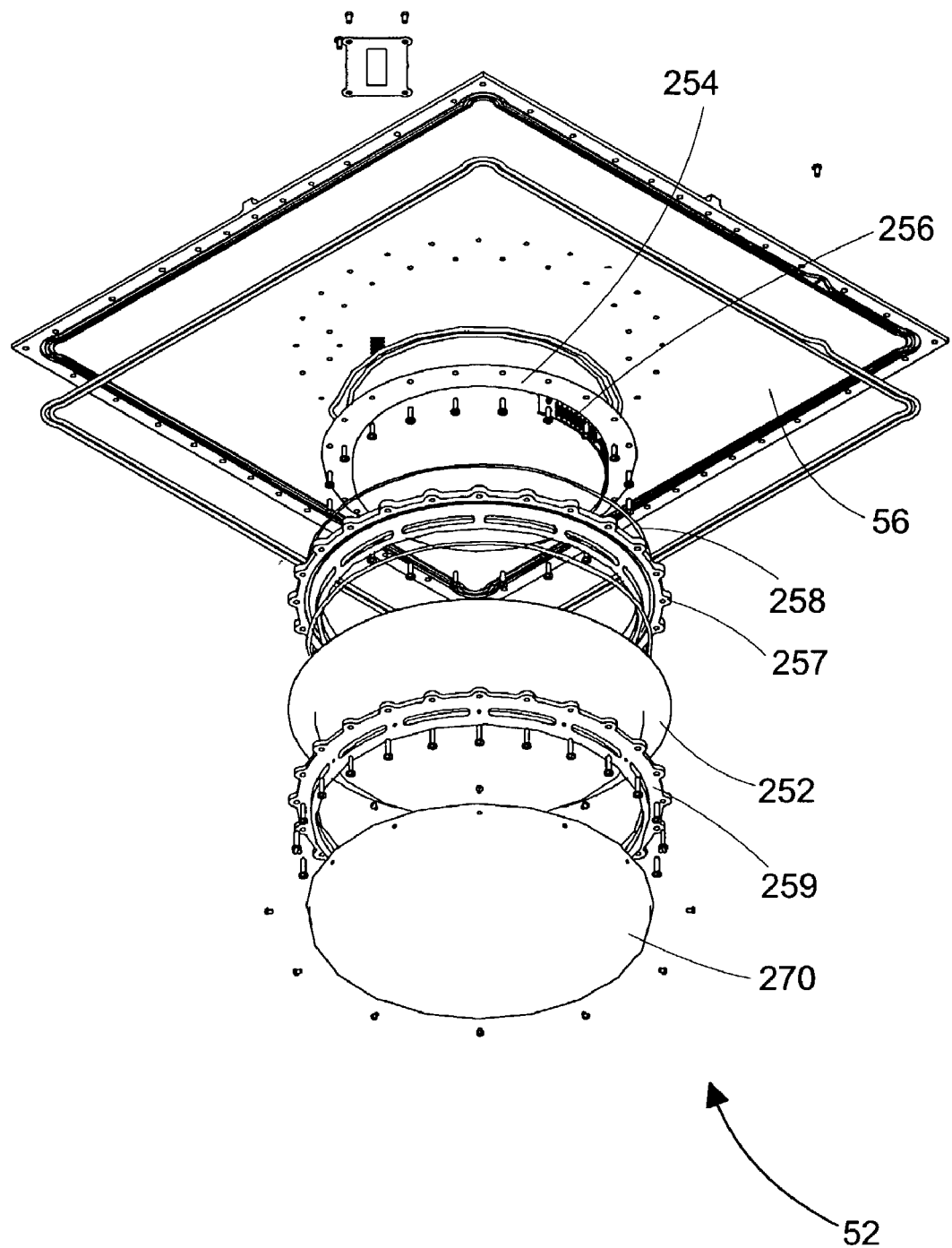
FIG. 16 is an exploded isometric view of the vapor containment system of the invention.

The vent system 52 in FIG. 16 is comprised of two subsystems: a primary hydrophobic membrane 252 and neutralizing housing 254. Because the inner housing 50 provides two levels of containment for hazardous materials and the vent system 52 is incorporated into the inner housing 50, the vent system 52 provides two hydrophobic membranes 252 to contain hazardous materials within the specimen volume 51, one in each subsystem. The primary hydrophobic membrane 252 contains liquid and solid contaminants within the specimen volume 51 while allowing gases to vent. The neutralizing housing 254 provide redundant containment of liquid and solid materials with a secondary hydrophobic membrane 256 (located at the entrance to the neutralizing housing 254), and neutralizes any vaporous formaldehyde contained in the air being vented to the cabin. FIGS. 1 and 3 show the vent system 52 attached to the inner housing lid 56. There are two independent vent systems 52 in the ADF device, one on each lid 56.

FIG. 16 shows the exploded isometric view of the vent system 52. The base plate 257 with the bottom O-ring 258 is installed to the inner housing lid 56 with three fasteners to reduce the number of parts installed at once. A second O-ring is then laid in the base plate O-ring groove. The primary hydrophobic membrane 252 is draped over the base plate 257 and pulled taut across the top of the base plate (in a manner similar to the use of plastic cling wrap or saran wrap). The primary hydrophobic membrane 252 is folded in up to four places along the sides to take up the slack. A fastening ring 259 and a preferable 50-mesh screen 270 is then placed over the top of the primary hydrophobic membrane 252, and the whole unit is fastened to the lid 56 with #4-40 fasteners. The screen 270 is attached to the fastening ring 259 using #4-40 fasteners.

The primary hydrophobic membrane 252 is protected from tearing using a 50-mesh stainless steel screen 270 to prevent penetrations from items that may be floating in the low gravity environment. The membrane 252 is sandwiched between the base plate 257 and the fastening ring 259. O-ring seals 258 are located between the base plate 257 and the inner housing lid 56 and the fastening ring 259 and the base plate 257. Tests have shown that the system will seal and hold pressure to 5 psid with four 1-inch folds in the primary hydrophobic membrane 252 using a 1.5 inch fastener spacing and 4 in-lb torque on the fasteners. This system should not see a pressure differential across it.

The neutralizing granules in the neutralizing housing 254 ("MM1000") potassium permanganate have two functions: redundant containment of hazardous materials and neutralization of the formaldehyde vapor. The secondary hydrophobic membrane 256 is a containment for the neutralizing granules. It contains the liquid and solid hazardous materials inside the specimen volume 51, but allows vapors to vent through the neutralizing housing 254. The secondary membrane 256 provides containment redundancy should the primary membrane 252 rupture or leak.

The neutralizing granules remove vaporous formaldehyde from the air (FIG. 16). Once air passes through the hydrophobic membranes 252 and 256, it flows through the neutralizing granules that are capable of neutralizing 100% of the paraformaldehyde in the ADF device 10 (assuming all the paraformaldehyde is converted to vapor).

Figure 17:
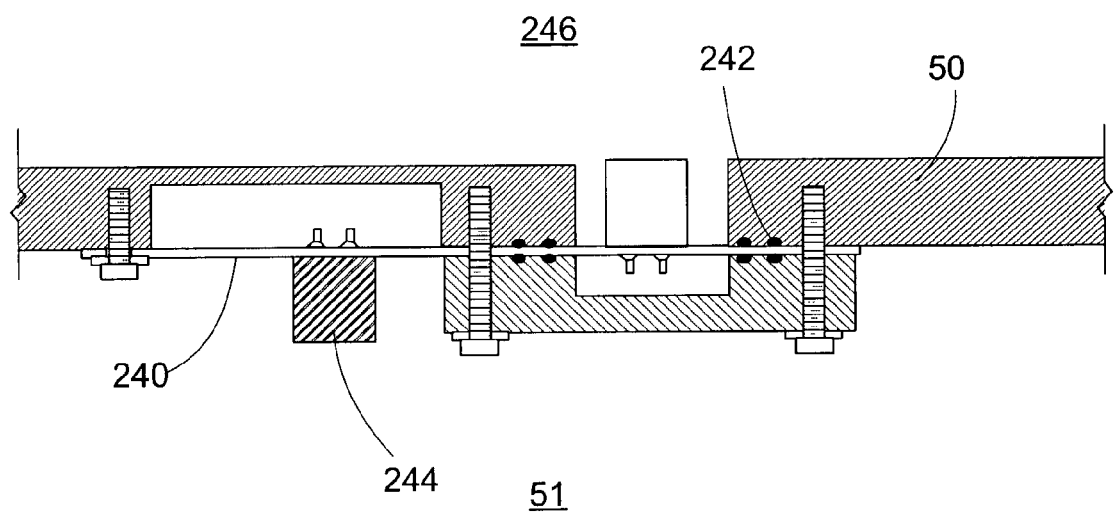
FIG. 17 is an elevation view of a double-containment input/output passthrough electronic board.

The pass-through connections are made via a circuit board 240, which allows for a double O-ring seal 242 and eliminates the need for sealed connectors. FIG. 17 represents the design for sealing electronic connections between the specimen volume boards 244 and the electronics enclosure 246. Traces are on internal layers of the circuit board 240, and there are no vias (holes) in the area around the O-ring seals 242.

All space hardware must be fire-suppressible. Prior art devices typically provide merely an opening or through-hole in the hardware that can receive a $CO_2$ or halon canister. A crew member must manually attach the canister to the through-hole, and dispense the contents to suppress the fire.

The device 10 of the preferred embodiment is advantageously fitted with a unique fire-suppression system that is in place on the hardware and maintains the two levels of containment. A crew member merely has to operate a lever that automatically activates the fire suppression system. This system is rack-mounted and does not violate the containment levels.

Figure 18:
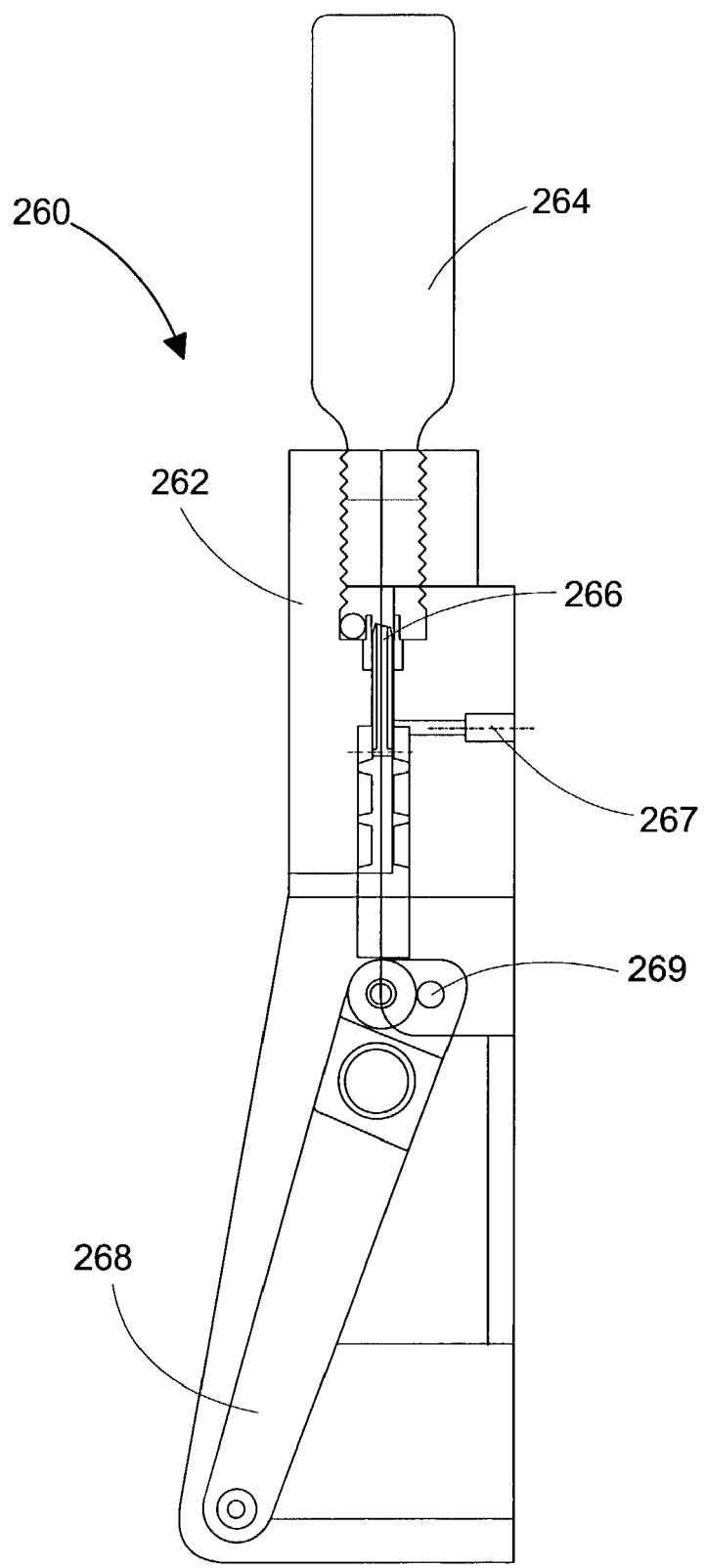
FIG. 18 is an assembly diagram of the manual fire-suppression system of the invention.

In the preferred embodiment shown in FIG. 1, a fire-suppression system 260 shown in FIG. 18 is included that consists of a holder 262 for at least one standard pressurized carbon dioxide cartridge 264 and a lever-operated self sealing penetrator 266 for perforating the neck of the carbon-dioxide cartridge 264 and allowing vaporized carbon dioxide to escape via port 267 into the interior of the electronics housing frame 220 and the inner housing 50. Manually operating lever 268 rotates cam 269 to actuate the penetrator 266. The unit will operate with two cartridges or one cartridge and a closeout plug.

As stated at the outset, devices according to the present invention may utilize samples other than eggs, such as liquids in vials. In addition, although the preferred embodiments are directed to devices designed for use in low gravity situations, the invention contemplates devices that are not so constrained. Persons of ordinary skill in the art will appreciate the obvious modifications that can be made to devices for use in terrestrial-based applications (such as using these devices for injection systems as part of a laboratory robot). Other uses of the invention 10 apparent to those practiced in the art are considered to be covered by this patent.

The following examples illustrate but a few of the uses for the device 10.

EXAMPLE 1

In tests of the device 10, thirty-six egg samples 12 from *Coturnix coturnix* japonica were inserted into egg holders 20. The device 10 was positioned so that the carousels 30 rotated in a vertical plane continuously at 77.3 rpm. A program was written for 12 days of operation with each egg sample 12 being rotated through 180° at one-hour intervals.

After four days of operation six egg samples 12 were robotically injected with 30 mL of 4% neutral buffered formalin solution. After seven days of operation, an additional twelve egg samples 12 were robotically injected with 30 ml of 4% neutral buffered formalin solution as well. The results showed that 50% of the egg samples 12 were unbroken after the test, and post-fixation examination revealed that 89% of the egg samples 12 developed normally.

EXAMPLE 2

Figure 15:
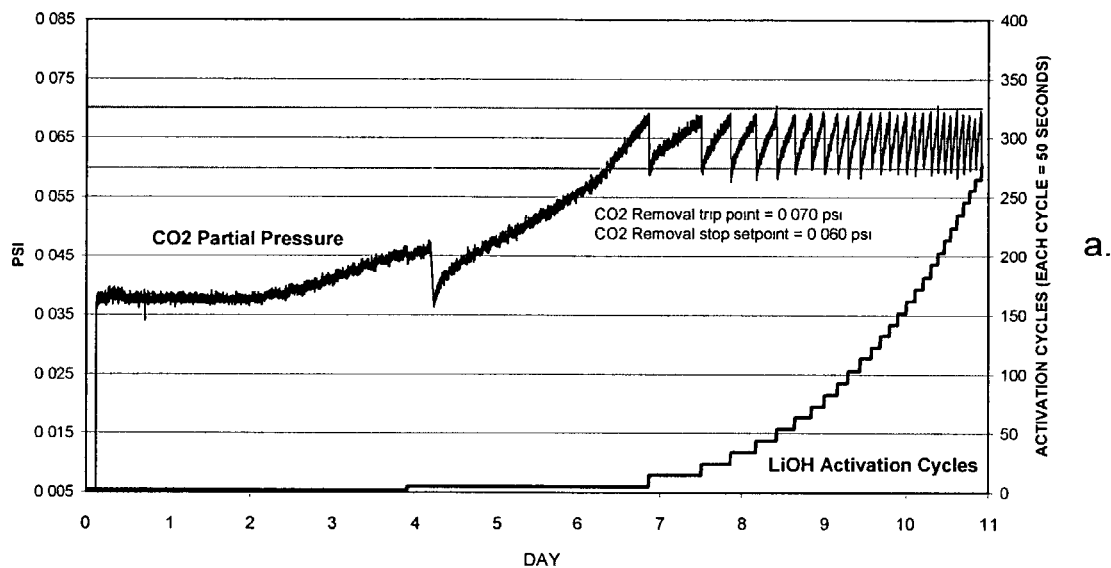
FIG. 15 is a display of operational and environmental data produced by the computer-based monitoring system of the invention.
Figure 15:
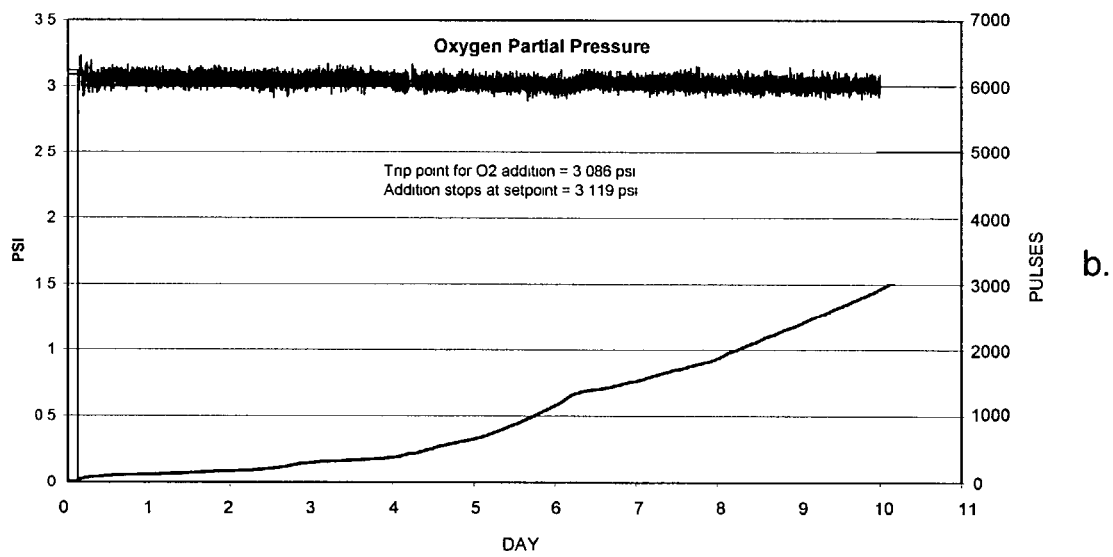

The device 10 was operated for 11 days with thirty-six egg samples 12 incubating in the sample volume. As time passed oxygen ($O_2$) was depleted, and carbon dioxide ($CO_2$) was produced. The graphs in FIG. 15 represent the ability of the ADF device 10 to maintain constant $O_2$ partial pressure and acceptable limits of $CO_2$ during this period, especially the latter half of the period when metabolic activity was increasing. The graph of FIG. 15a indicates that $CO_2$ was regulated within acceptable limits by the opening, upon demand, of the valve that circulates air through the LiOH carbon dioxide removal system. The graph of FIG. 15b indicates that $O_2$ was maintained at constant (physiological) pressure by the opening, upon demand, of the valve that releases 30% $O_2$ air from the air tank.

While there has been described and illustrated particular embodiments of a novel device and method for centrifugation and robotic manipulation of incubating egg samples, it will be apparent to those skilled in the art that variations and modifications are possible without deviating from the broad spirit and principle of the present invention, which shall be limited solely by the scope of the claims appended hereto.

What is claimed is:

1. A apparatus for centrifugation and manipulation of samples comprising:
   a housing defining an environment therein;
   at least one carousel rotatably coupled via a carousel drive subsystem to said housing through a first axis through said at least one carousel to enable an infinite number of inertial acceleration conditions within said environment;
   a plurality of sample holder assemblies, each of said sample holder assemblies having a respective longitudinal centroidal axis therethrough, coupled to said carousel and disposed at a distance from said first axis, each sample holder assembly rotatably coupled to said carousel via a sample turning subsystem for rotation about each of said respective longitudinal centroidal axes therethrough; and
   a control computer interfaced with said carousel drive subsystem and said sample turning subsystem and at least one output device, and driven by software that activates and deactivates said carousel drive subsystem and said sample turning subsystem at times and for durations and speeds defined by a user wherein said carousel drive subsystem further comprises a carousel base mounted to said housing and a carousel plate rotatably coupled to said carousel base by a drive mechanism.

2. The apparatus for centrifugation and manipulation of samples of claim 1 wherein said carousel plate further comprises a hub disposed about a main drive gear, wherein said hub is connected to a periphery by a plurality of spokes.

3. The apparatus for centrifugation and manipulation of samples of claim 2 wherein said hub portion interfaces said carousel base via a slip ring and said main drive gear.

4. The apparatus for centrifugation and manipulation of samples of claim 3 wherein said periphery is mounted to said carousel base by a clamped bearing preventing out of plane rotation of said carousel plate.

5. The apparatus for centrifugation and manipulation of samples of claim 4 wherein said main drive mechanism engages said main drive gear and imparts torque to said hub, said torque being transmitted to said periphery via said spokes thereby rotating said periphery about said first axis and imparting centripetal acceleration to said periphery.

6. The apparatus for centrifugation and manipulation of samples of claim 5 wherein said torque rotates said periphery at speeds in the range of approximately 0 revolutions per minute to approximately 100 revolutions per minute.

7. The apparatus for centrifugation and manipulation of samples of claim 1 wherein said plurality of sample holder assemblies are coupled to said carousel at said carousel plate.

8. The apparatus for centrifugation and manipulation of samples of claim 7 wherein said sample turning subsystem further comprises a gear motor and mating gears coupled to each of said plurality of sample holder assemblies.

9. The apparatus for centrifugation and manipulation of samples of claim 8 wherein each of said mating gears coupled to each of said plurality of sample holder assemblies are coupled such that each adjacent sample holder assembly of said plurality of sample holder assemblies are rotatable about said respective longitudinal centroidal axes upon rotation of a lead sample holder by said gear motor.

10. The apparatus for centrifugation and manipulation of samples of claim 9 wherein each of said sample holder assemblies of said plurality of sample holder assemblies further comprises a sample isolator, a sample holder containing said sample isolator and an endcap assembly, a septum coupled to said endcap, a needle hole in said septum, a sample holder bearing with locking plate surrounding said sample holder, and a sample holder assembly bearing surrounding said sample holder bearing.

11. The apparatus for centrifugation and manipulation of samples of claim 10 wherein said sample isolator further comprises an annular ring having a first surface and a second surface and at least two standoff legs for positioning said sample within said sample holder a predetermined distance away from said endcap assembly wherein said at least two standoff legs extend from said first surface said annular ring at connection points defined from a reference origin at approximately 0 degrees and approximately 180 degrees about a perimeter of said annular ring, each of said at least two standoff legs extending in a first radial direction from said annular ring.

12. The apparatus for centrifugation and manipulation of samples of claim 11 wherein said sample isolator further comprises at least two resiliently opposed sidearms having an inner surface and an outer surface extending from said second surface of said annular ring in a second direction from said annular ring opposite said first direction.

13. The apparatus for centrifugation and manipulation of samples of claim 12 wherein said at least two resiliently opposed sidearms are located at approximately 90 degrees and approximately 270 degrees from said reference origin about said perimeter of said annular ring.

14. The apparatus for centrifugation and manipulation of samples of claim 12 wherein said sidearms further comprise pads attached to said inner surface of said sidearms for resiliently engaging a sample therebetween.

15. The apparatus for centrifugation and manipulation of samples of claim 10 wherein said sample holder further comprises an open cylindrical body defining an interior environment and having a first end and a second end and a cylindrical surface therearound defining a sample holder diameter, and having at least one opening through said cylindrical surface and O-rings fitted around said opening to provide gas exchange between said sample and said interior environment when said sample holder is open, and to seal said interior environment when said sample holder is closed.

16. The apparatus for centrifugation and manipulation of samples of claim 15 wherein said sidearms further comprise pads attached to said outer surface of said sidearms for engaging said cylindrical surface in said interior environment.

17. The apparatus for centrifugation and manipulation of samples of claim 10 wherein said endcap assembly further comprises an endcap having locking tabs extending from a perimeter thereof, and having an upper surface and a lower surface and a hydrophobic vent therethrough, wherein said lower surface comprises a disc with air channels therein, at least one O-ring at a perimeter of said lower surface of said endcap and at least one hydrophobic membrane for sealingly engaging said lower surface of said endcap to said first end of said sample holder upon engaging said locking tabs into mating openings in said sample holder.

18. The apparatus for centrifugation and manipulation of samples of claim 15 wherein said sample holder bearing further comprises an open cylindrical body having a first end and a second end and a cylindrical surface therearound defining a sample holder bearing diameter, said sample holder bearing diameter being greater than said sample holder diameter, and wherein said cylindrical surface engages said O-rings for sealing said sample holder.

19. The apparatus for centrifugation and manipulation of samples of claim 15 wherein said locking plate has an upper surface and a lower surface and a diameter greater than said sample holder diameter and wherein said lower surface receives said endcap assembly.

20. The apparatus for centrifugation and manipulation of samples of claim 19 wherein said locking plate is mounted to said sample holder bearing allowing said sample holder to rotate within said sample holder bearing.

21. The apparatus for centrifugation and manipulation of samples of claim 15 wherein said sample holder assembly bearing further comprises an annular member having a cylindrical surface defining an inner diameter and further comprising mounting tabs extending radially from said cylindrical surface.

22. The apparatus for centrifugation and manipulation of samples of claim 21 wherein said mounting tabs are coupled to said carousel plate.

23. The apparatus for centrifugation and manipulation of samples of claim 21 wherein said cylindrical surface of said sample holder assembly bearing receives said cylindrical body of said sample holder and allows said sample holder to rotate within said cylindrical surface.

24. The apparatus for centrifugation and manipulation of samples of claim 1 wherein said apparatus further comprises a chemical process system for conducting procedures on said samples.

25. The apparatus for centrifugation and manipulation of samples of claim 24 wherein said chemical process system further comprises an injection reservoir, an injection pump coupled to said injection reservoir, and an injection head coupled to said injection pump.

26. The apparatus for centrifugation and manipulation of samples of claim 25 wherein said injection head is mounted to said carousel base.

27. The apparatus for centrifugation and manipulation of samples of claim 25 wherein said injection reservoir further comprises a flexible container of liquid surrounded by a solid container.

28. The apparatus for centrifugation and manipulation of samples of claim 25 wherein said injection pump is a peristaltic pump controlled by a stepper motor with programmable controls.

29. The apparatus for centrifugation and manipulation of samples of claim 25 wherein said injection head further comprises a stepper motor, a lead screw coupled to said stepper motor, a needle carrier connected to said lead screw, a needle mounted to said needle carrier, and a locking plate having a needle hole therein and O-rings located on either side of said needle hole, said locking plate being slidably coupled to said injection head.

30. The apparatus for centrifugation and manipulation of samples of claim 29 wherein a first switch and a second switch are coupled to said injection head to detect positions of said carousel plate.

31. The apparatus for centrifugation and manipulation of samples of claim 30 wherein a third switch and a fourth switch are coupled to said injection head to contact said bottom of said sample holder bearing.

32. The apparatus for centrifugation and manipulation of samples of claim 31 wherein a fifth switch is coupled to said injection head to detect a needle extended situation wherein said injection needle is fully extended.

33. The apparatus for centrifugation and manipulation of samples of claim 32 wherein a sixth switch is coupled to said injection head to detect a needle and locking plate retracted condition wherein said injection needle and said injection locking plate are fully retracted.

34. The apparatus for centrifugation and manipulation of samples of claim 33 wherein said control computer determines a desired sample holder of said plurality of sample holders to locate over said injection head, causes rotation of said carousel plate to cease, receives index information from said first switch and said second switch, determines said index information for said desired sample holder, activates said stepper motor to index said desired sample holder adjacent said injection head, and locks said desired sample holder into position.

35. The apparatus for centrifugation and manipulation of samples of claim 34 wherein said stepper motor drives said lead screw, thereby driving said needle carrier toward said sample holder, wherein said engagement plate travels concurrently therewith.

36. The apparatus for centrifugation and manipulation of samples of claim 35 wherein said third switch and said fourth switch actuate to cease travel of said needle carrier upon full engagement of said locking plate with said sample holder.

37. The apparatus for centrifugation and manipulation of samples of claim 36 wherein said gear motor rotates said sample holder bearing to close said sample holder within said sample holder bearing and expose said hydrophobic membrane while said injection head holds said sample holder stationary.

38. The apparatus for centrifugation and manipulation of samples of claim 37 wherein said third switch disengages upon detecting a cutout in said egg holder bearing.

39. The apparatus for centrifugation and manipulation of samples of claim 38 wherein said injection head indexes said injection needle through said needle hole in said septum into said sample.

40. The apparatus for centrifugation and manipulation of samples of claim 39 wherein said fifth switch indicates needle engagement by actuating against said needle carrier.

41. The apparatus for centrifugation and manipulation of samples of claim 40 wherein said injection pump activates upon needle engagement.

42. The apparatus for centrifugation and manipulation of samples of claim 41 wherein said stepper motor activates to turn said sample holder bearing to close said hydrophobic membrane.

43. The apparatus for centrifugation and manipulation of samples of claim 42 wherein said fourth switch detects a closed condition, thereby activating said stepper motor to retract said needle into said locking plate and retract said locking plate from said sample holder, thereby returning said needle hole to a sealed position between said two O-rings in said locking plate.

44. The apparatus for centrifugation and manipulation of samples of claim 43 wherein said sixth switch indicates that said needle and said locking plate are fully retracted, thus sending a signal to said control computer to allow said carousel plate to freely rotate.

45. The apparatus for centrifugation and manipulation of samples of claim 1 wherein said apparatus further comprises a humidity control system comprising a moisture delivery system and a moisture removal system and a humidity sensor.

46. The apparatus for centrifugation and manipulation of samples of claim 45 wherein said moisture delivery system further comprises a reservoir for holding water, a sponge within said environment, and flexible tubing coupling said flexible reservoir to said sponge via a pump.

47. The apparatus for centrifugation and manipulation of samples of claim 46 wherein said pump is activated to dispense water from said reservoir to said sponge when said humidity sensor detects a humidity level below a predetermined lower humidity set point.

48. The apparatus for centrifugation and manipulation of samples of claim 45 wherein said moisture removal system further comprises a desiccant canister having an entrance and an exit, a pump having a pump entrance and a pump exit wherein said pump entrance is open to said environment and wherein said pump exit is coupled to said entrance of said desiccant canister.

49. The apparatus for centrifugation and manipulation of samples of claim 48 wherein said exit of said desiccant canister further comprises a check valve.

50. The apparatus for centrifugation and manipulation of samples of claim 49 wherein said pump is activated to pull air from said environment into said pump entrance when said humidity sensor detects a humidity level above a predetermined upper humidity set point.

51. The apparatus for centrifugation and manipulation of samples of claim 1 wherein said apparatus further comprises an atmospheric control system.

52. The apparatus for centrifugation and manipulation of samples of claim 51 wherein said atmospheric control system further comprises an oxygen control system.

53. The apparatus for centrifugation and manipulation of samples of claim 52 wherein said oxygen control system further comprises an air tank containing air, an oxygen sensor to monitor oxygen concentration in said environment, and a solenoid valve connected to said air tank via tubing and to said control computer.

54. The apparatus for centrifugation and manipulation of samples of claim 53 wherein said solenoid valve operates to add a burst of oxygen into said environment upon receiving a signal from said computer controller when said oxygen sensor detects an oxygen concentration below a predetermined set point.

55. The apparatus for centrifugation and manipulation of samples of claim 54 wherein said atmospheric control system further comprises a carbon dioxide system.

56. The apparatus for centrifugation and manipulation of samples of claim 55 wherein said carbon dioxide system further comprises a canister containing lithium hydroxide, a pump connected to said canister, and a carbon dioxide sensor to monitor carbon dioxide concentration in said environment.

57. The apparatus for centrifugation and manipulation of samples of claim 56 wherein said pump activates when said carbon dioxide sensor detects a level of carbon dioxide in said air that is above a predetermined set point, and then draws said air from said environment into said canister whereby said lithium hydroxide converts carbon dioxide present in said air into solid lithium carbonate and water, and then discharges treated air back into said environment.

58. The apparatus for centrifugation and manipulation of samples of claim 1 wherein said apparatus further comprises a thermal control system.

59. The apparatus for centrifugation and manipulation of samples of claim 58 wherein said thermal control system further comprises at least one heat exchanger within said environment, a temperature sensor within said environment, a plurality of fans within said environment, and at least one exhaust opening through said housing, said at least one heat exchanger, temperature sensor, and plurality of fans coupled to said control computer to activate upon said temperature sensor detecting a temperature outside a predetermined range of acceptable temperatures within said environment.

60. The apparatus for centrifugation and manipulation of samples of claim 1 wherein said apparatus further comprises a fire suppression system.

61. The apparatus for centrifugation and manipulation of samples of claim 60 wherein said fire suppression system further comprises a holder for at least one pressurized carbon dioxide cartridge, a lever rotatably mounted to said holder in cooperation with a cam, said cam actuating a self-sealing penetrator upon rotation of said lever that penetrates said pressurized carbon dioxide canister thereby releasing contents into said environment.

62. The apparatus for centrifugation and manipulation of samples of claim 60 wherein said fire suppression system further comprises a holder for at least one pressurized carbon dioxide cartridge in an environment containing electronic components, a lever rotatably mounted to said holder in cooperation with a cam, said cam actuating a self-sealing penetrator upon rotation of said lever that penetrates said pressurized carbon dioxide canister thereby releasing contents into said environment.

63. An apparatus for centrifugation and manipulation of samples comprising:
  a housing defining an environment therein;
  at least one carousel rotatably coupled via a carousel drive subsystem to said housing through a first axis through said at least one carousel to enable an infinite number of inertial acceleration conditions within said environment;
  a plurality of sample holder assemblies, each of which having a respective longitudinal centroidal axis therethrough, coupled to said carousel and disposed at a distance from said first axis, each sample holder assembly rotatably coupled to said carousel via a sample turning subsystem for rotation about each of said respective longitudinal centroidal axes therethrough; and a control computer interfaced with said carousel drive subsystem and said sample turning subsystem and at least one output device, and driven by software that activates and deactivates said carousel drive subsystem and said sample turning subsystem at times and for durations and speeds defined by a user;

wherein said housing further comprises two levels of sealed containment and wherein electronic signals are passed through said two levels of sealed containment from an external connector to a circuit board thence along conductors printed on said circuit board thence to an internal connector having terminals electrically coupled thereto and connected to said conductors, said terminals being attached at through-holes in said circuit board and said through-holes sealed within the internal volume by a panel and two pairs of captured O-rings, thereby providing two levels of containment for vapors, liquids and solids.

64. An apparatus for centrifugation and manipulation of samples comprising:

a housing defining an environment therein;

at least one carousel rotatably coupled via a carousel drive subsystem to said housing through a first axis through said at least one carousel to enable an infinite number of inertial acceleration conditions within said environment;

a plurality of sample holder assemblies, each of which having a respective longitudinal centroidal axis therethrough, coupled to said carousel and disposed at a distance from said first axis, each sample holder assembly rotatably coupled to said carousel via a sample turning subsystem for rotation about each of said respective longitudinal centroidal axes therethrough; and a control computer interfaced with said carousel drive subsystem and said sample turning subsystem and at least one output device, and driven by software that activates and deactivates said carousel drive subsystem and said sample turning subsystem at times and for durations and speeds defined by a user;

wherein said housing further comprises a hydrophobic membrane subsystem and a neutralizing housing, said hydrophobic membrane subsystem further comprising a primary hydrophobic membrane that contains liquid and solid materials and a secondary hydrophobic membrane located at an entrance to said neutralizing housing, and wherein said neutralizing housing provides redundant containment of liquid and solid materials and further neutralizes vapors being vented from said environment.

* * * * *